United States Patent
Aoyama et al.

(10) Patent No.: US 10,558,263 B2
(45) Date of Patent: Feb. 11, 2020

(54) IMAGE DIAGNOSIS ASSISTANCE APPARATUS, CONTROL METHOD THEREOF, AND PROGRAM

(71) Applicant: CANON KABUSHIKI KAISHA, Tokyo (JP)

(72) Inventors: Gakuto Aoyama, Kyoto (JP); Masahiro Yakami, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 396 days.

(21) Appl. No.: 15/305,913

(22) PCT Filed: May 13, 2015

(86) PCT No.: PCT/JP2015/064392
§ 371 (c)(1),
(2) Date: Oct. 21, 2016

(87) PCT Pub. No.: WO2015/174548
PCT Pub. Date: Nov. 19, 2015

(65) Prior Publication Data
US 2017/0045938 A1    Feb. 16, 2017

(30) Foreign Application Priority Data

May 16, 2014    (JP) ................................ 2014-102725

(51) Int. Cl.
*G06F 3/01*    (2006.01)
*A61B 6/00*    (2006.01)
*G06F 19/00*    (2018.01)

(52) U.S. Cl.
CPC .............. *G06F 3/013* (2013.01); *A61B 6/466* (2013.01); *G06F 19/321* (2013.01)

(58) Field of Classification Search
CPC ........ G06F 3/013; G06F 19/321; A61B 6/466
See application file for complete search history.

(56) References Cited

U.S. PATENT DOCUMENTS 6,317,510 B1 * 11/2001 Murakami ........... G06K 9/3233
382/132
6,381,339 B1 * 4/2002 Brown .................... G06F 3/013
382/100

(Continued)

FOREIGN PATENT DOCUMENTS

JP    H02-196383 A    8/1990
JP    H11-244280 A    9/1999

(Continued)

OTHER PUBLICATIONS

International Search Report and Written Opinion issued in International Application No. PCT/JP2015/064392 dated Sep. 10, 2015.

*Primary Examiner* — Amare Mengistu
*Assistant Examiner* — Crystal Mathews
(74) *Attorney, Agent, or Firm* — Venable LLP

(57) ABSTRACT

An image diagnosis assistance apparatus displays, on a display screen, a tomographic image obtained from a three-dimensional medical image, and detects a gaze position of a user on the display screen. The image diagnosis assistance apparatus determines an observed region in the tomographic image based on the detected gaze position, and identifies the observed region in the three-dimensional medical image based on the region determined to have been observed in the tomographic image.

14 Claims, 20 Drawing Sheets

(56) References Cited

U.S. PATENT DOCUMENTS

| | | | |
|---|---|---|---|
| 7,043,067 B2 | 5/2006 | Murakami | |
| 7,327,505 B2* | 2/2008 | Fedorovskaya | G06F 3/011 358/527 |
| 7,668,285 B2* | 2/2010 | Mukumoto | G06T 11/005 378/4 |
| 7,738,684 B2* | 6/2010 | Kariathungal | G06F 3/013 382/128 |
| 8,020,993 B1* | 9/2011 | Fram | G06F 3/013 351/200 |
| 8,885,882 B1* | 11/2014 | Yin | G06F 3/00 382/103 |
| 9,652,032 B2* | 5/2017 | Mitchell | G06F 3/013 |
| 2002/0159624 A1 | 10/2002 | Murakami | |
| 2004/0103111 A1* | 5/2004 | Miller | G02B 27/017 |
| 2006/0139319 A1* | 6/2006 | Kariathungal | G06F 3/013 345/156 |
| 2006/0238877 A1* | 10/2006 | Ashkenazi | G02B 27/0093 359/630 |
| 2008/0112602 A1* | 5/2008 | Azemoto | G06T 5/008 382/128 |
| 2009/0257550 A1* | 10/2009 | Moriya | G06T 19/00 378/4 |
| 2009/0289895 A1* | 11/2009 | Nakada | G06F 3/013 345/157 |
| 2011/0006978 A1* | 1/2011 | Yuan | G06F 3/013 345/156 |
| 2011/0115883 A1* | 5/2011 | Kellerman | G06F 3/012 348/46 |
| 2011/0270123 A1* | 11/2011 | Reiner | A61B 3/113 600/558 |
| 2011/0310006 A1* | 12/2011 | Edwards | A61B 3/113 345/156 |
| 2013/0051646 A1* | 2/2013 | Nakano | G06T 7/0012 382/131 |
| 2013/0106692 A1* | 5/2013 | Maizels | G06F 3/011 345/156 |
| 2013/0342539 A1* | 12/2013 | Khan | G06T 11/00 345/440 |
| 2014/0146156 A1* | 5/2014 | Strombom | A61B 3/113 348/78 |
| 2015/0213725 A1* | 7/2015 | Huntley | A61B 5/168 345/156 |
| 2016/0026245 A1* | 1/2016 | Mantiuk | G06F 3/013 382/103 |
| 2018/0314327 A1* | 11/2018 | Digirolamo | G06K 9/3233 |

FOREIGN PATENT DOCUMENTS

| | | |
|---|---|---|
| JP | 2002-320603 A | 11/2002 |
| JP | 2007-050045 A | 3/2007 |
| JP | 2007-319327 A | 12/2007 |
| WO | 2012/164430 A2 | 12/2012 |

* cited by examiner

| $O_t$ | $O_{tp}$ | $O_{tl}/O_{tw}$ | $O_{tb}$ | $O_{th}$ |
|---|---|---|---|---|
| $O_1$ | (200, 250, 150) | 35/350 | 138 | 50 |
| $O_2$ | (200, 250, 150) | 35/350 | 138 | 50 |
| $O_3$ | (200, 230, 150) | 35/350 | 0 | -500 |
| $O_4$ | (210, 230, 150) | 35/350 | 0 | -700 |
| $O_5$ | (220, 200, 150) | 35/350 | 0 | -900 |
| $O_6$ | NULL | NULL | NULL | NULL |
| $O_7$ | NULL | NULL | NULL | NULL |
| $O_8$ | (220, 200, 150) | -600/1500 | 76 | -900 |
| $O_9$ | (220, 200, 150) | -600/1500 | 76 | -900 |
| ... | | | | |

| (200, 250, 150) |
| (220, 200, 150) |
| ... |

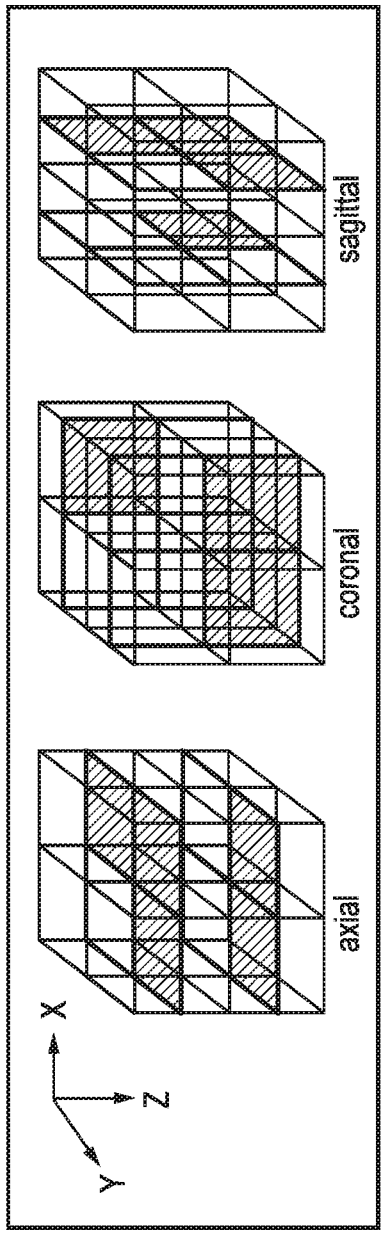
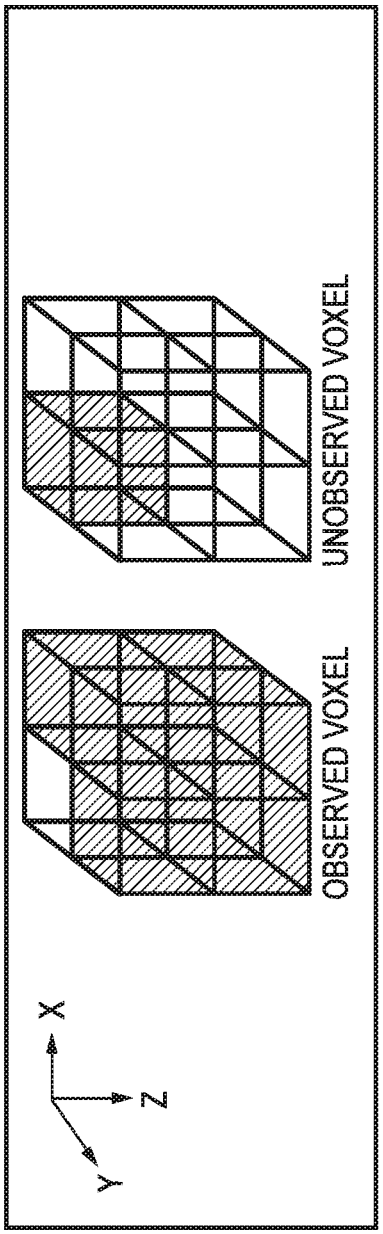
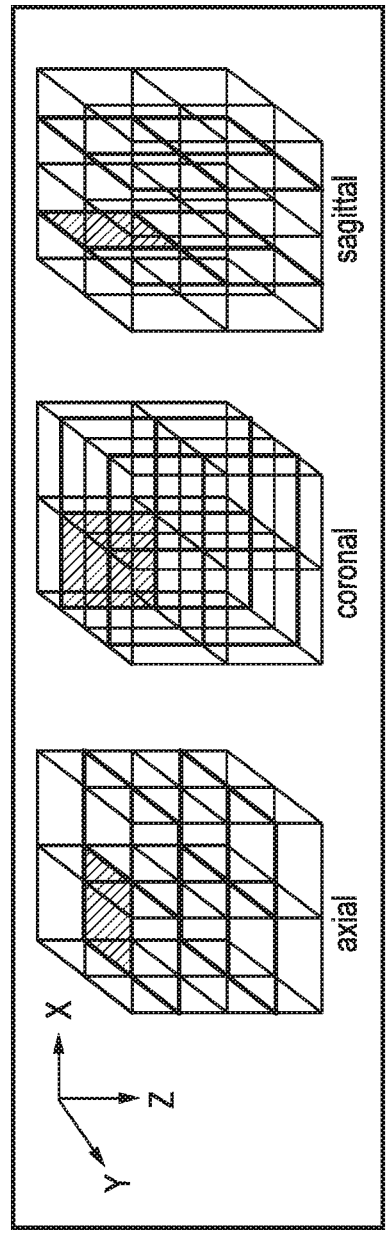
FIG. 9A
FIG. 9B
FIG. 9C

FIG. 9D

| $O_t$ | $O_{td}$ | $O_{tp}$ |
|---|---|---|
| $O_1$ | axial | (2, 1, 1) |
| $O_2$ | axial | (2, 2, 1) |
| $O_3$ | axial | (1, 2, 1) |
| $O_4$ | axial | (2, 2, 1) |
| $O_5$ | axial | (2, 2, 2) |
| $O_6$ | axial | (1, 2, 2) |
| $O_7$ | coronal | (1, 2, 2) |
| $O_8$ | coronal | (2, 2, 2) |
| $O_9$ | sagittal | (2, 2, 2) |
| $O_{10}$ | sagittal | (2, 1, 2) |
| $O_{11}$ | sagittal | (1, 1, 2) |
| $O_{12}$ | sagittal | (2, 1, 2) |
| $O_{13}$ | sagittal | (2, 1, 1) |
| $O_{14}$ | coronal | (2, 1, 1) |
| $O_{15}$ | axial | (2, 1, 1) |
| $O_{16}$ | other | NULL |
| $O_{17}$ | axial | (2, 1, 1) |
| $O_{18}$ | axial | (2, 2, 1) |
| $O_{19}$ | other | NULL |
| $O_{20}$ | other | NULL |

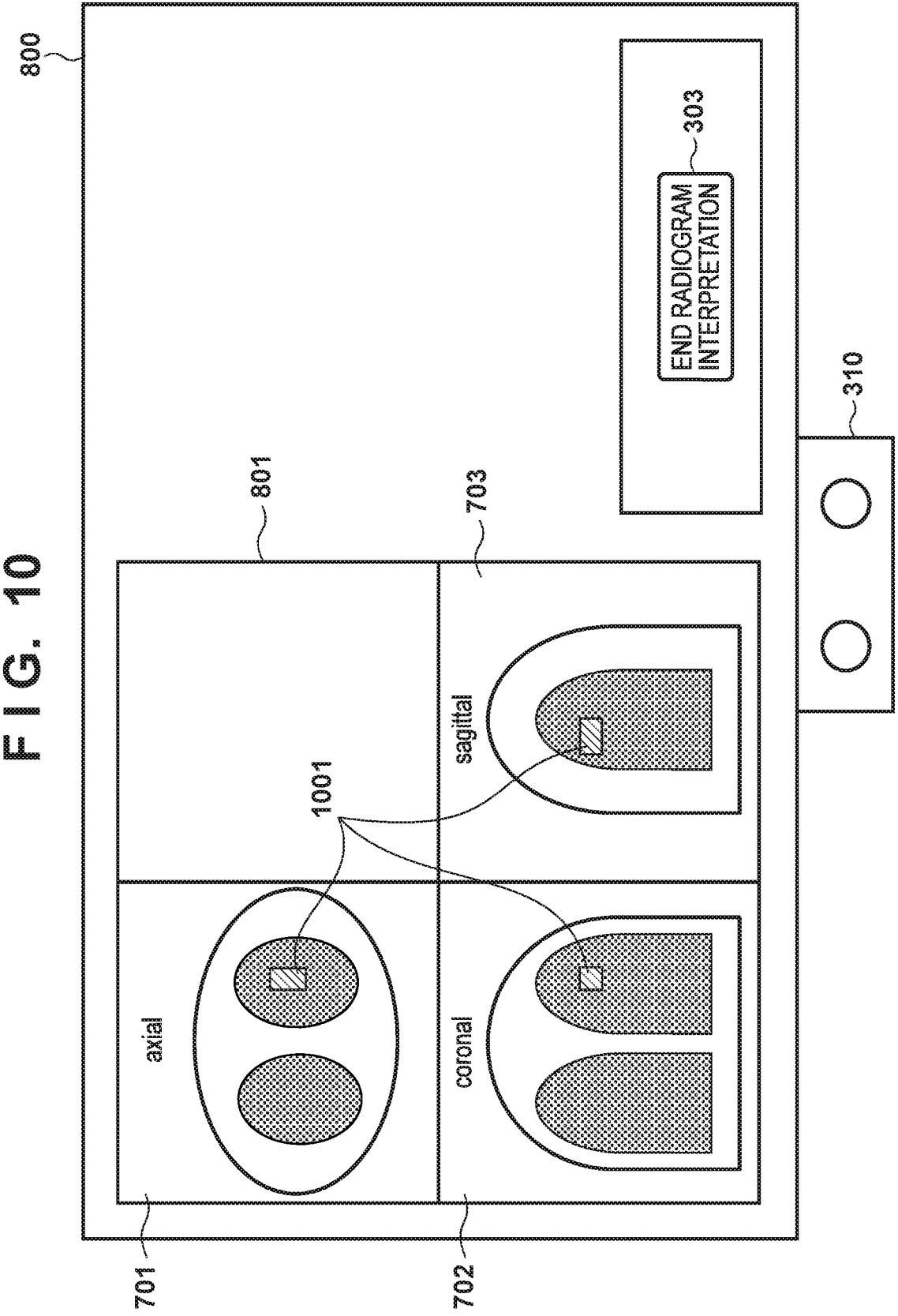

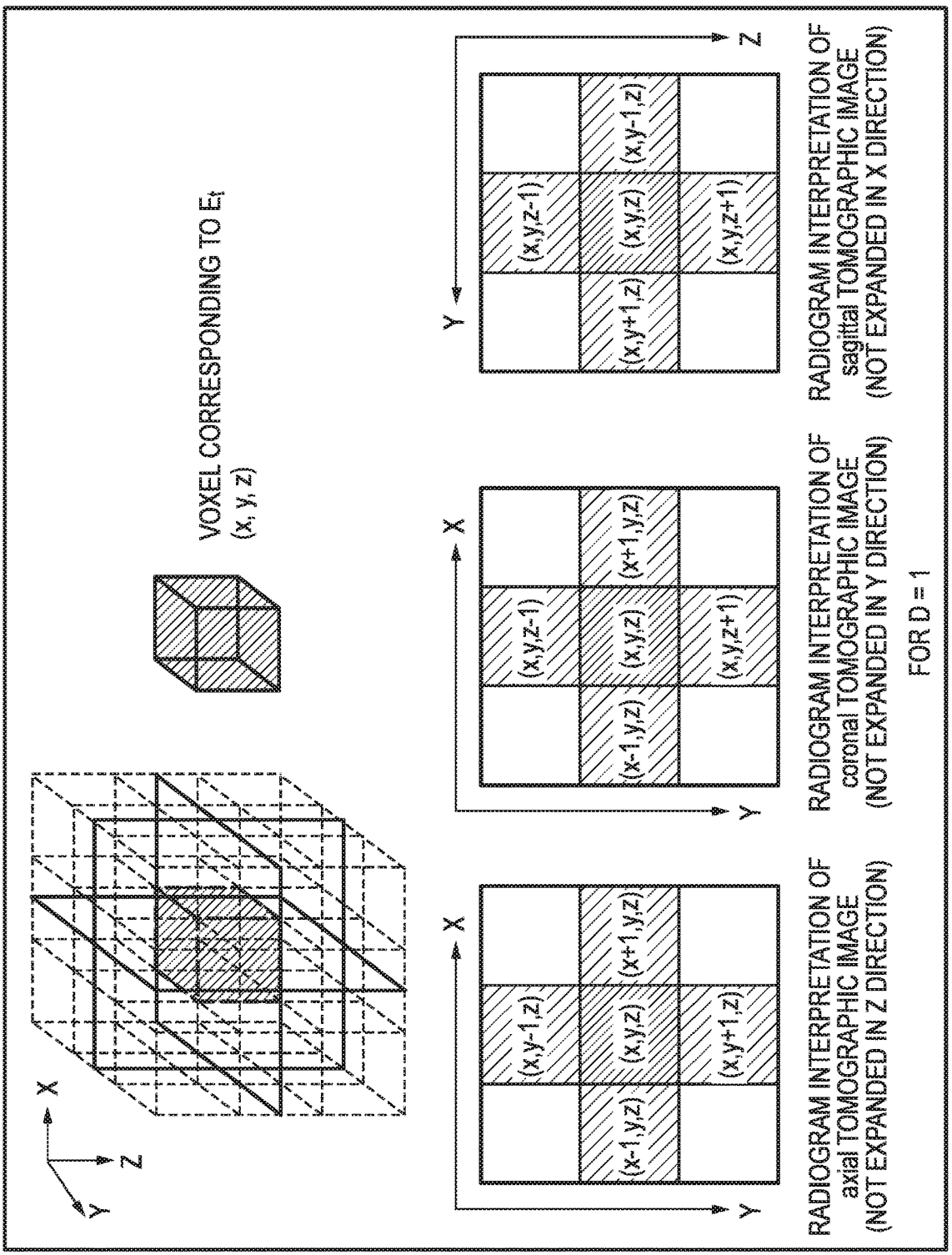

FIG. 12A

| $O_t$ | $O_{td}$ | $O_{tp}$ | $O_t$ | $O_{td}$ | $O_{tp}$ |
|---|---|---|---|---|---|
| $O_1$ | axial | (2, 1, 1) | $O_{201}$ | coronal | (1, 2, 1) |
| $O_2$ | axial | (2, 2, 1) | $O_{202}$ | coronal | (1, 1, 1) |
| $O_3$ | axial | (2, 2, 1) | $O_{203}$ | coronal | (1, 1, 1) |
| $O_4$ | axial | (2, 2, 1) | $O_{204}$ | coronal | (1, 1, 1) |
| $O_5$ | axial | (2, 2, 1) | $O_{205}$ | coronal | (1, 1, 1) |
| $O_6$ | axial | (2, 2, 1) | $O_{206}$ | sagittal | (1, 1, 1) |
| $O_7$ | axial | (2, 2, 1) | $O_{207}$ | sagittal | (1, 1, 1) |
| $O_8$ | axial | (2, 2, 1) | $O_{208}$ | sagittal | (1, 1, 1) |
| $O_9$ | axial | (2, 2, 1) | $O_{209}$ | sagittal | (1, 1, 1) |
| $O_{10}$ | axial | (2, 2, 1) | $O_{210}$ | sagittal | (1, 1, 1) |
| $O_{11}$ | axial | (2, 2, 1) | $O_{211}$ | sagittal | (1, 1, 1) |
| $O_{12}$ | axial | (2, 2, 1) | $O_{212}$ | sagittal | (1, 1, 1) |
| $O_{13}$ | axial | (1, 2, 1) | $O_{213}$ | sagittal | (1, 1, 1) |
| $O_{14}$ | axial | (1, 2, 1) | $O_{214}$ | sagittal | (1, 2, 1) |
| $O_{15}$ | axial | ... | $O_{215}$ | sagittal | (1, 2, 1) |

O Axial : (2, 2, 1)  OBSERVATION REGION INFORMATION

FIG. 12B

| axial | axial | axial | axial | coronal | coronal | coronal | sagittal | sagittal | sagittal | sagittal | axial | axial |
|---|---|---|---|---|---|---|---|---|---|---|---|---|
| (2,1,1) | (1,2,1) | (1,2,2) | (2,1,2) | (2,1,1) | (1,1,1) | (2,2,2) | (2,1,2) | (1,1,2) | (2,1,2) | (1,2,1) | (2,1,2) | (2,2,1) |

OBSERVED REGION IN RESPECTIVE TOMOGRAPHIC IMAGES

FIG. 12C

| (1,1,1) | (1,2,1) | (1,2,2) | (2,1,1) | (2,1,2) | (2,2,1) | (2,2,2) |
|---|---|---|---|---|---|---|

OBSERVED REGION IN THREE-DIMENSIONAL IMAGE DATA

F I G. 15

| axial | coronal | sagittal | layer |
|---|---|---|---|
| UNOBSERVED | UNOBSERVED | UNOBSERVED | NOT GENERATED |
| UNOBSERVED | UNOBSERVED | OBSERVED | NOT GENERATED |
| UNOBSERVED | OBSERVED | UNOBSERVED | NOT GENERATED |
| UNOBSERVED | OBSERVED | OBSERVED | GENERATED |
| OBSERVED | UNOBSERVED | UNOBSERVED | NOT GENERATED |
| OBSERVED | OBSERVED | OBSERVED | GENERATED |
| OBSERVED | OBSERVED | UNOBSERVED | GENERATED |
| OBSERVED | OBSERVED | OBSERVED | GENERATED |

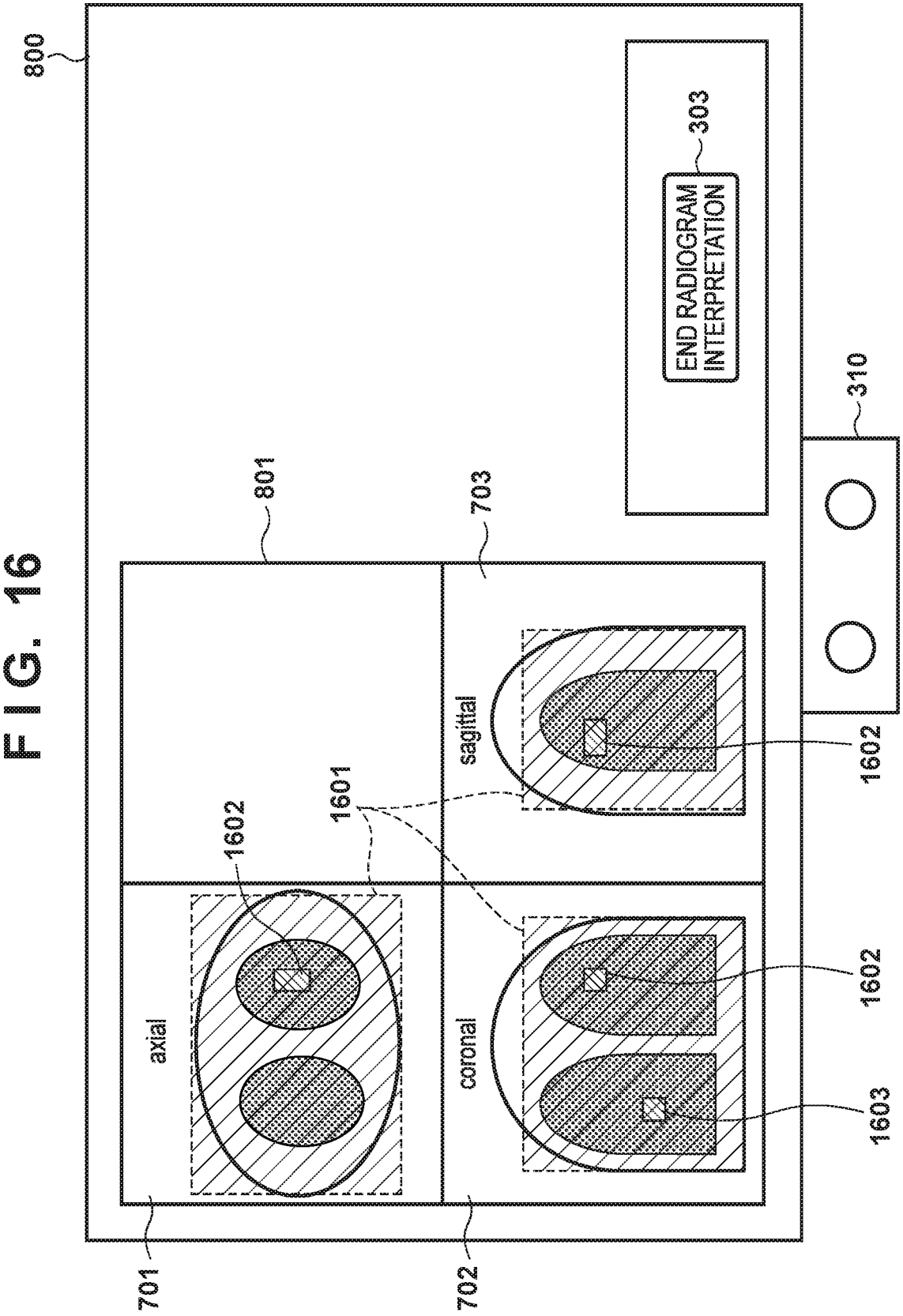

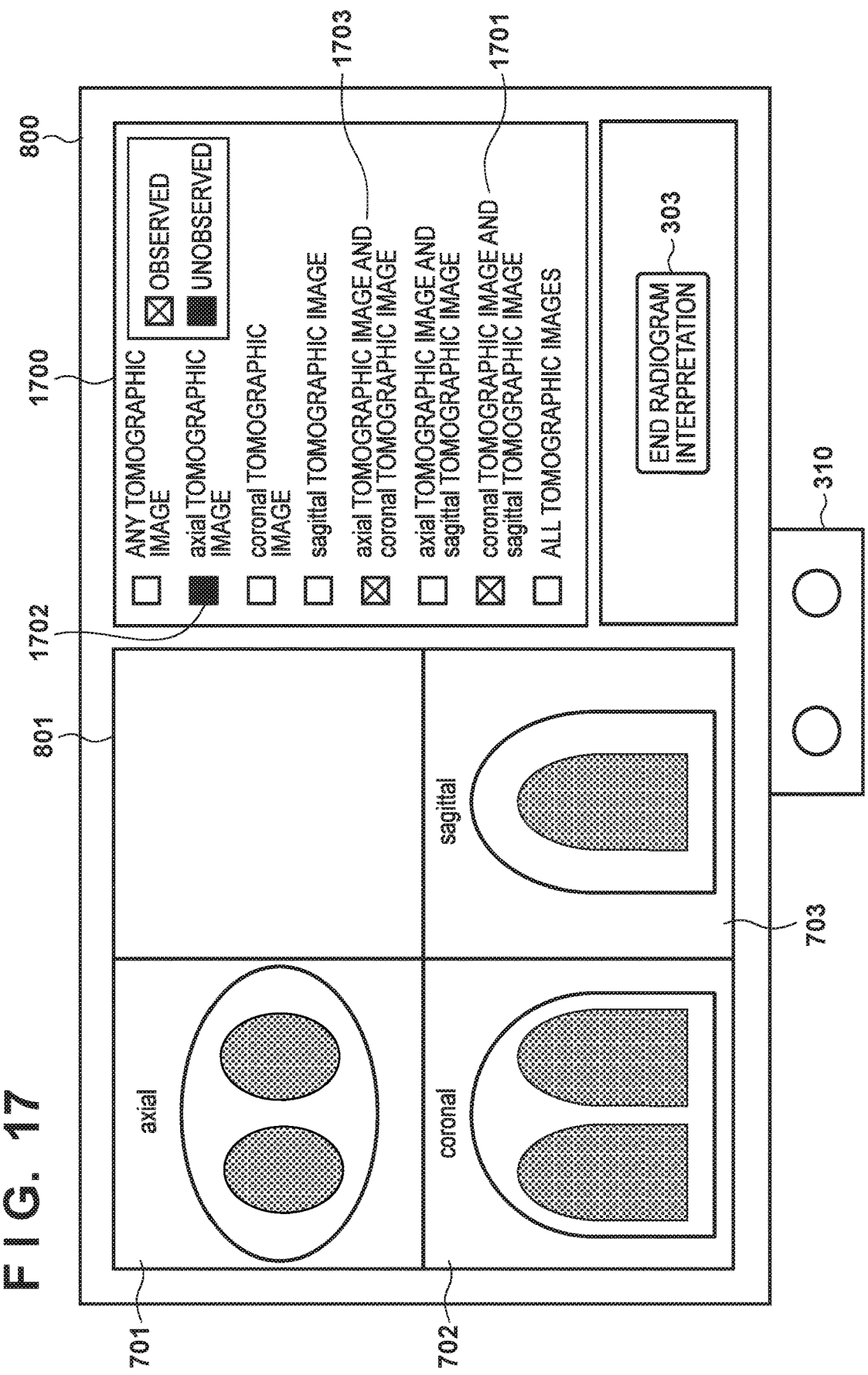

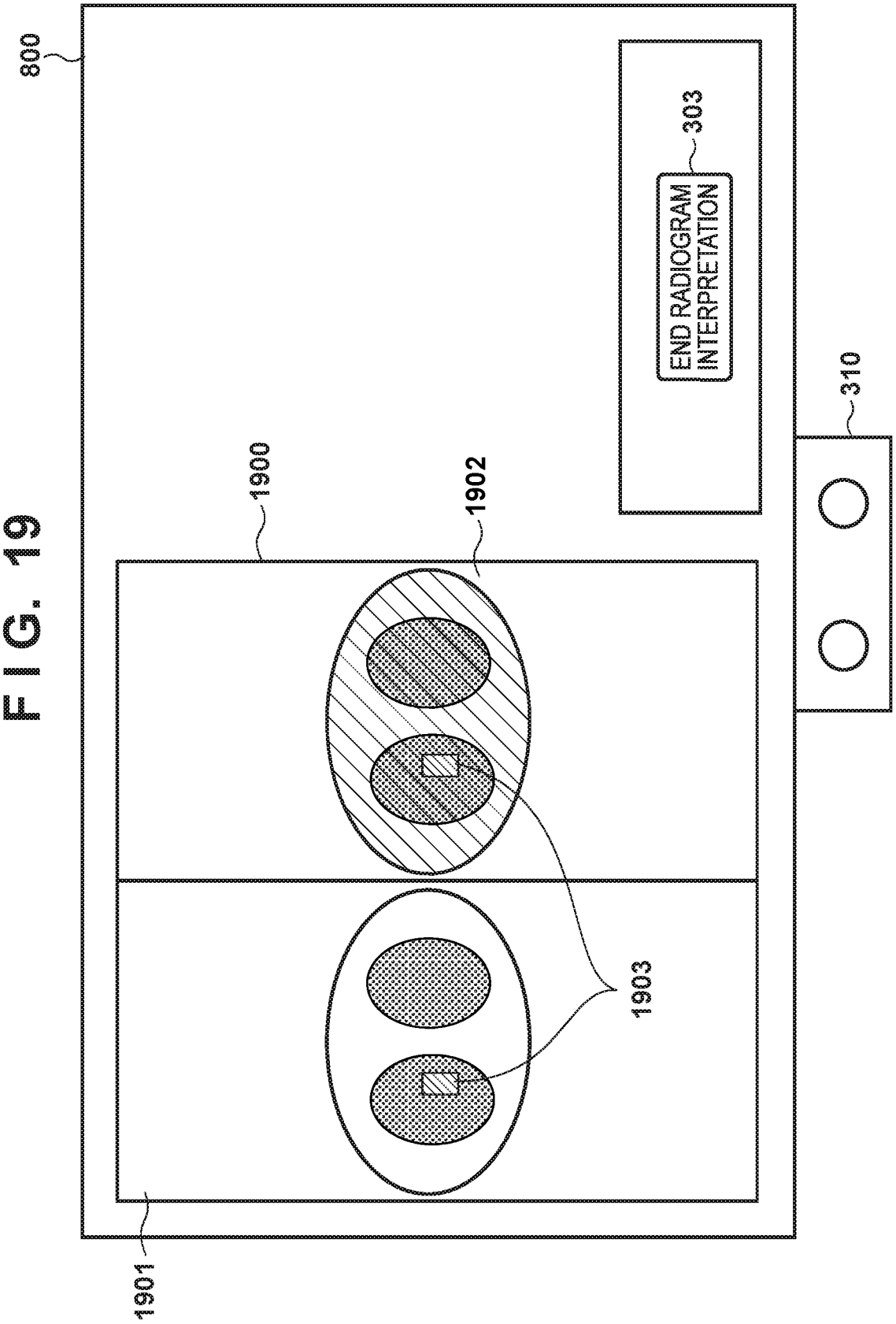

IMAGE DIAGNOSIS ASSISTANCE APPARATUS, CONTROL METHOD THEREOF, AND PROGRAM

TECHNICAL FIELD

The present invention relates to an image diagnosis assistance apparatus, a control method thereof, and a program.

BACKGROUND ART

At the medical site, a medical imaging apparatus such as an X-ray CT apparatus, MRI apparatus, or PET apparatus captures a three-dimensional medical image formed from a plurality of tomographic images. When performing radiogram interpretation of these medical images and performing image diagnosis, a doctor displays (scrolls and displays) a plurality of tomographic images while successively switching them, observes the entire three-dimensional medical image, and finds out and evaluates an abnormal shadow in the image. To perform more accurate image diagnosis, a so-called MPR (Multi-Planar Reconstruction) method is sometimes used. According to this method, a three-dimensional medical image is reconstructed into an image (to be referred to as a tomographic image hereinafter) of a slice in an arbitrary direction (to be referred to as a tomographic direction hereinafter), and the reconstructed three-dimensional medical image is displayed. By using this method, tomographic images in a plurality of tomographic directions are created, displayed, and used for radiogram interpretation.

Recently, an increase in the number of images of medical images and complication of them are proceeding owing to an increase in the number of patients against the background of an aging society and an increase in the amount of information along with medical advance. Therefore, the burden on a doctor in radiogram interpretation operations is rapidly increasing, and there is a fear of an increase in misses or evaluation errors of abnormal shadows (to be referred to as radiogram interpretation omission hereinafter).

Japanese Patent Laid-Open No. 2007-319327 (to be referred to as literature 1 hereinafter) discloses a technique of recording the operation of a system and sight line information of a radiogram interpreter in time series at the time of radiogram interpretation. According to this technique, by measuring and recording the sight line of the radiogram interpreter to a radiogram interpretation target image, the radiogram interpreter can identify an observed region and an unobserved region, and can point out radiogram interpretation omission of the unobserved region.

However, in literature 1, an observed region and an unobserved region are merely identified on an image displayed by the system based on the operation record and sight line information of the system. For example, as a result of interpreting an image displayed in an improper display state, some organs and abnormal shadows may not be displayed clearly and may not be interpreted appropriately. In literature 1, even when such an improperly displayed image is observed, it is determined from sight line information that the region has been observed.

SUMMARY OF INVENTION

Embodiments of the present invention disclose a diagnosis assistance apparatus and diagnosis assistance method capable of appropriately identifying an observed region and an unobserved region at the time of radiogram interpretation.

According to one aspect of the present invention, there is provided an image diagnosis assistance apparatus comprising: display means for displaying, on a display screen, a tomographic image obtained from a three-dimensional medical image; detection means for detecting a gaze position of a user on the display screen; determination means for determining an observed region in the tomographic image based on the gaze position detected by the detection means; and identification means for identifying the observed region in the three-dimensional medical image based on the observed region in the tomographic image that has been determined by the determination means.

Also, according to another aspect of the present invention, there is provided a control method of an image diagnosis assistance apparatus, comprising: a display step of displaying, on a display screen, a tomographic image obtained from a three-dimensional medical image; a detection step of detecting a gaze position of a user on the display screen; a determination step of determining an observed region in the tomographic image based on the gaze position detected in the detection step; and an identification step of identifying the observed region in the three-dimensional medical image based on the observed region in the tomographic image that has been determined in the determination step.

Further features of the present invention will become apparent from the following description of exemplary embodiments with reference to the attached drawings.

BRIEF DESCRIPTION OF DRAWINGS

FIGS. 9A to 9D are views showing an explanation of an identification condition according to the fourth embodiment;

FIG. 10 is a view showing an example of superposition and display of a marker according to the fourth embodiment;

FIG. 11 is a view for explaining expansion of sight line information;

FIGS. 12A to 12C are tables for explaining a modification of the fourth embodiment;

FIG. 15 is a table for explaining the generation condition of a marker according to the fifth embodiment;

FIG. 16 is a view showing an example of superposition and display of a marker according to the fifth embodiment;

FIG. 17 is a view showing an example of a GUI according to the sixth embodiment;

FIG. 19 is a view showing an example of superposition and display of a marker according to the seventh embodiment.

DESCRIPTION OF EMBODIMENTS

Several embodiments of the present invention will now be described with reference to the accompanying drawings. Note that the scope of the present invention is not limited to the following exemplified embodiments and illustrative examples.

First Embodiment

An image diagnosis assistance apparatus according to the first embodiment obtains medical information (for example, information of a medical image or electronic medical chart) regarding the case of a diagnosis target, and input information from a user (for example, sight line information of a user or operation information of a GUI), and performs diagnosis assistance regarding this case. The following description assumes a case in which a chest X-ray CT image is handled as an example of a three-dimensional medical image. A case in which radiogram interpretation is performed using an axial image will be mainly explained. Needless to say, the assistance target is not limited to this, and any of the following embodiments is merely an example for explaining processing of the image diagnosis assistance apparatus.

Figure 1:
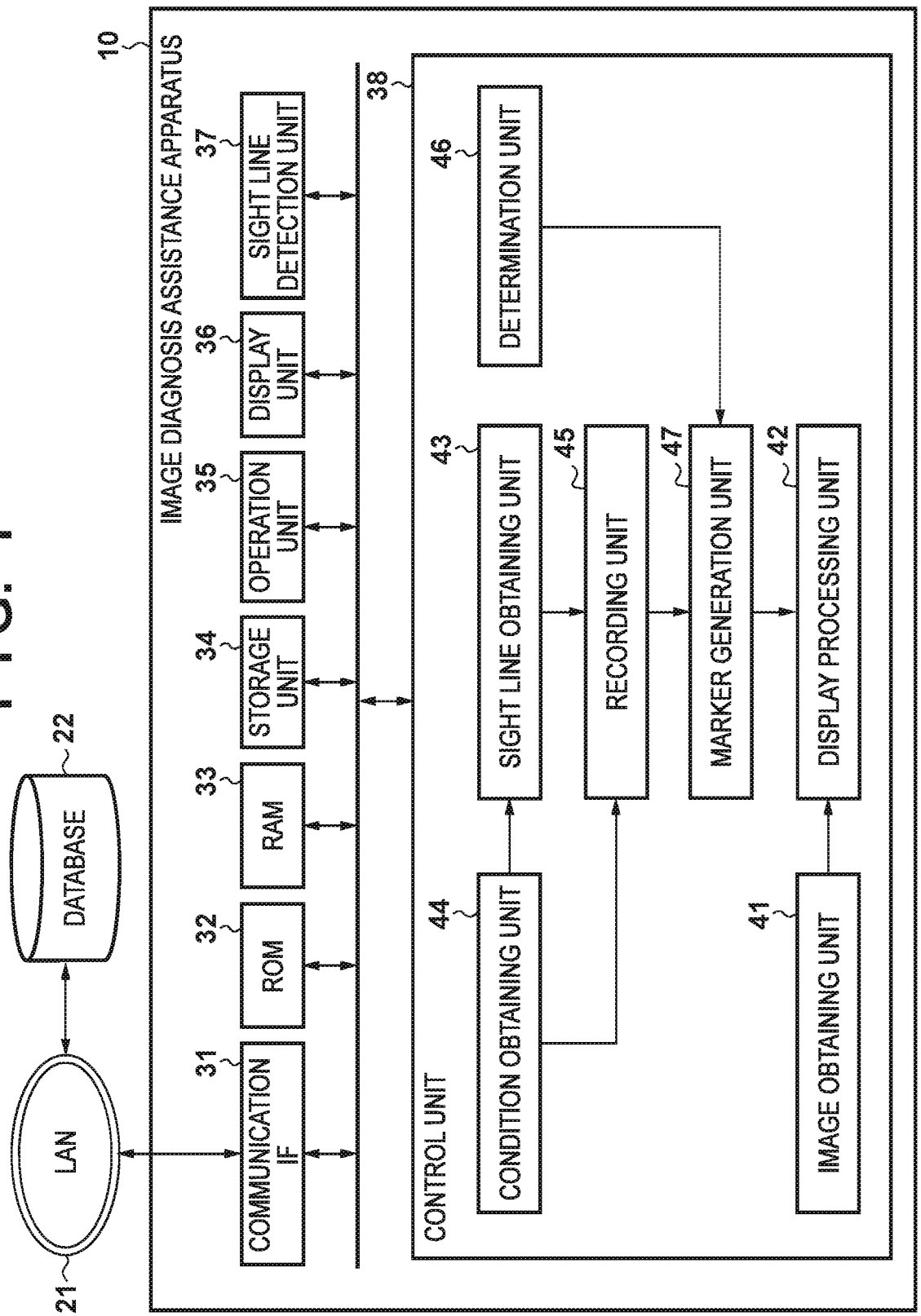
FIG. 1 is a block diagram showing an example of the arrangement of an image diagnosis apparatus according to the first to seventh embodiments.

FIG. 1 is a block diagram showing the overall arrangement of an image diagnosis assistance system including an image diagnosis assistance apparatus 10 according to this embodiment. The image diagnosis assistance system includes the image diagnosis assistance apparatus 10 and a database 22. The image diagnosis assistance apparatus 10 and the database 22 are connected via a LAN (Local Area Network) 21 serving as a communication means so that they can communicate with each other. The database 22 manages data such as a medical image. The image diagnosis assistance apparatus 10 obtains, via the LAN 21, a medical image managed in the database 22. The image diagnosis assistance apparatus 10 includes, as its functional components, a communication interface (to be referred to as a communication IF 31 hereinafter), a ROM (Read Only Memory) 32, a RAM (Random Access Memory) 33, a storage unit 34, an operation unit 35, a display unit 36, a sight line detection unit 37, and a control unit 38.

The communication IF 31 is implemented by a LAN card or the like, and controls communication between an external apparatus (for example, the database 22) and the image diagnosis assistance apparatus 10 via the LAN 21. The ROM 32 is implemented by a nonvolatile memory or the like, and stores various programs and the like. The RAM 33 is implemented by a volatile memory or the like, and temporarily stores various kinds of information. The storage unit 34 is implemented by, for example, an HDD (Hard Disk Drive) and stores various kinds of information. The operation unit 35 is implemented by a keyboard and mouse or the like, and inputs an instruction from a user into the apparatus. The display unit 36 is implemented by a display or the like, and displays various kinds of information to a user (for example, a doctor).

The sight line detection unit 37 is implemented by, for example, a video camera capable of synchronous imaging from a plurality of viewpoints or eye tracker (sight line tracking apparatus). For example, the sight line detection unit 37 detects sight line information of a user by imaging the face and eye of the user from a plurality of viewpoints and performing predetermined image recognition processing on stereo images obtained by imaging. The sight line detection unit 37 obtains the orientation of the face of the user, the positions and moving direction of the irises of both the eyes, and the like in a three-dimensional coordinate system, thereby detecting sight line information representing a gaze position of the user with respect to the display unit 36. The sight line information is generally obtained as information representing a portion (pixel) looked on the display screen of the display unit 36.

The control unit 38 is implemented by a CPU (Central Processing Unit) or the like, and comprehensively controls processing in the image diagnosis assistance apparatus 10. The control unit 38 includes, as its functional components, an image obtaining unit 41, a display processing unit 42, a sight line obtaining unit 43, a condition obtaining unit 44, a recording unit 45, a determination unit 46, and a marker generation unit 47.

The image obtaining unit 41 obtains the three-dimensional medical image of a diagnosis target from the database 22 via the communication IF 31 and the LAN 21, and outputs it to the display processing unit 42. The display processing unit 42 displays, on the display unit 36, the medical image obtained by the image obtaining unit 41. The display processing unit 42 superposes and displays, on the medical image on the display unit 36, a marker generated by the marker generation unit 47 to be described later.

The sight line obtaining unit 43 obtains sight line information detected by the sight line detection unit 37, and outputs it to the recording unit 45. The condition obtaining unit 44 obtains the display condition of a medical image output to the display unit 36, and outputs it to the recording unit 45. The display condition is information representing a range used for display on the display screen out of the entire range of pixel values used in an apparatus that captured a medical image, and details of the display condition will be described later. By using the sight line information obtained by the sight line obtaining unit 43 and the display condition obtained by the condition obtaining unit 44, the recording unit 45 associates a position on a medical image that corresponds to a position on the screen where sight line information has been detected, with the display condition and the density (luminance) on the screen, and records them in, for example, the storage unit 34. These data corresponding to the sight line information (gaze position) will be called observation region information. The observation region information is recorded as time-series information. Details of the observation region information will be described later. The recorded observation region information is output to the marker generation unit 47.

The determination unit 46 determines whether radiogram interpretation has ended, and notifies the marker generation unit 47 of the determination result. The marker generation unit 47 generates a marker to be displayed on an image, by using the observation region information recorded by the recording unit 45, and outputs it to the display processing unit 42. In this embodiment, it is determined based on the observation region information whether a region observed by the user in a tomographic image has been displayed in a proper display state (for example, display luminance). At least some of the components of the control unit 38 may be implemented as independent devices, or software that implements each function. This embodiment assumes that each component is implemented by software.

Figure 2:
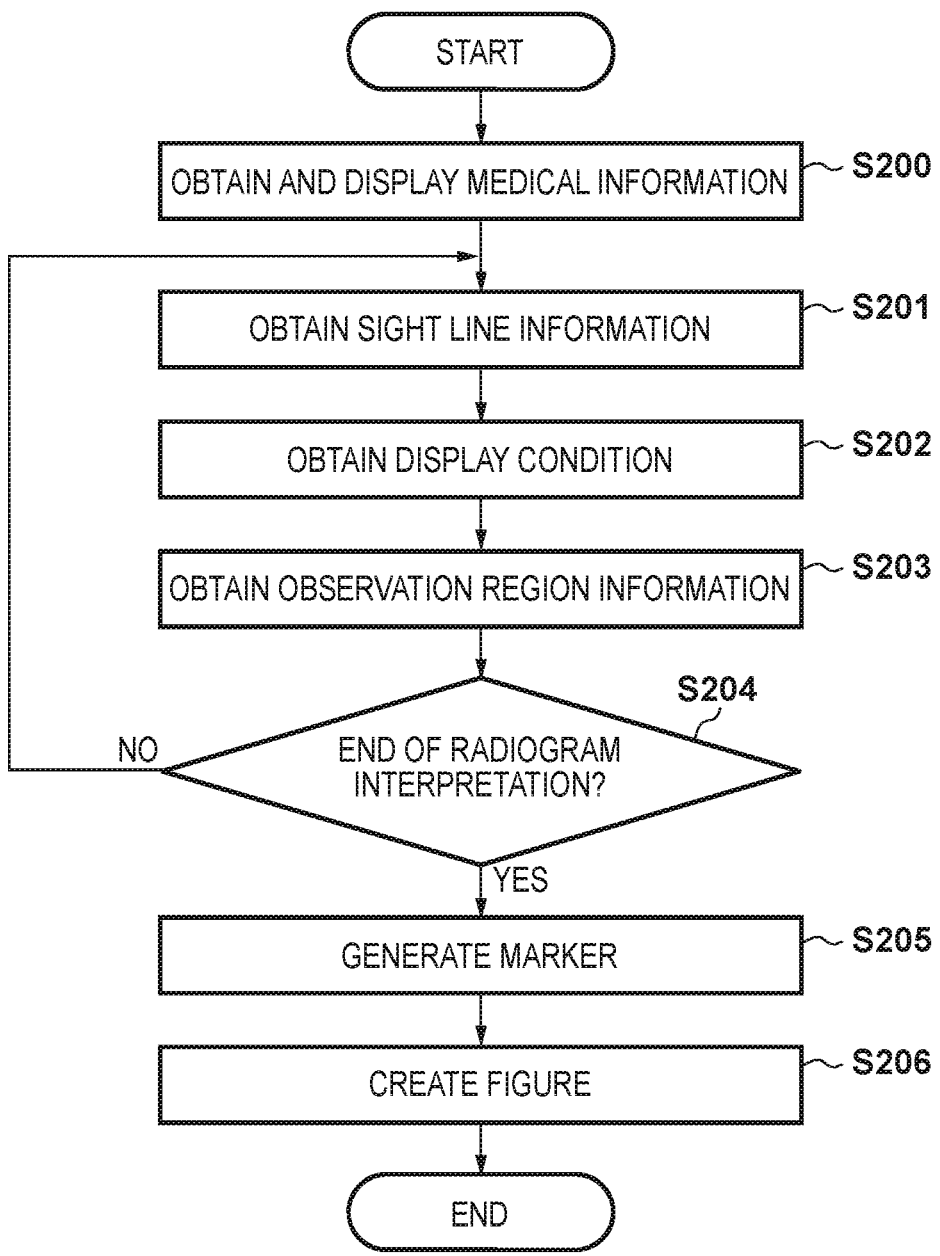
FIG. 2 is a flowchart for explaining overall processing according to the first to third embodiments.

Next, overall processing to be performed by the control unit 38 according to this embodiment will be explained with reference to the flowchart of FIG. 2. In the following description, the pixels of the display unit 36 are represented in an M-N coordinate system, and the voxels of a three-dimensional medical image are represented in an X-Y-Z coordinate system. Also, in the following description, detection of the sight line by the sight line detection unit 37 is executed at a predetermined sampling rate (for example, 0.1 sec), and the sight line is detected as sight line information. $E_t(e_{tm}, e_{tn})$ (t=1, 2, . . . ) represents sight line information (that is, information of a pixel looked on the display unit 36) at a given time point. $e_{tm}$ represents an M-coordinate on the display unit 36, and $e_{tn}$ represents an N-coordinate on the display unit 36. When the position of the detected sight line falls outside the display unit 36, the sight line information becomes NULL.

In this embodiment, a CT value (pixel value) is assigned as signed 16 bits to each voxel of a medical image. That is, when an apparatus that captured a medical image is, for example, a CT apparatus, the entire range of pixel values is represented by signed 16 bits, and the display condition represents a range used for display on the display screen out of the entire range. In this embodiment, the display condition has two parameters, that is, the window level (to be referred to as WL hereinafter) and the window width (to be referred to as WW hereinafter). WL and WW are parameters necessary to convert a specific CT value range (WL±WW/2) into a luminance displayable on the display unit 36. WL indicates the center value of a CT value range to be displayed, and WW is a value indicating the CT value range to be displayed (that is, WW>0).

Generally, the display unit 36 often gives a display using an unsigned 8-bit (256-tone) grayscale. In this case, luminance conversion (tone conversion) of the CT value using the display condition can be given by:

$$\begin{cases} 0 & \text{if } CT \text{ value} < WL - WW/2 \\ 255 & \text{if } CT \text{ value} > WL + WW/2 \\ \left[\dfrac{\{CT \text{ value} - (WL - WW/2)\} * 255}{WW}\right] & \text{otherwise} \end{cases} \quad (1)$$

where [X] is the Gaussian symbol. 0 represents the minimum value of the luminance displayable on the display unit 36, and 255 represents the maximum value of the luminance.

By this tone conversion, the radiogram interpreter can interpret a medical image at a tone corresponding to a display condition under which he/she wants to perform radiogram interpretation. For example, WL −600/WW 1500 is used as the display condition when the radiogram interpreter wants to interpret the lung field (lung field condition), WL 35/WW 350 is used when he wants to interpret a soft tissue (mediastinal condition), and WL 350/WW 1500 is used when he wants to interpret a bone (bone condition). As represented by conditional expression (1), when the CT value takes a value outside a desired CT value range, the luminance always takes 0 or 255 regardless of the distance from the desired CT value range. For example, in the case of the mediastinal condition (WL 35/WW 350), the desired CT value range is from −140 to 210, but the display luminance is 0 regardless of whether the CT value is −141 or −1000.

Observation region information $O_t$ includes the position (to be referred to as Pos hereinafter and represented by $O_{tp}(o_{tx}, o_{ty}, o_{tz})$) of a voxel in a three-dimensional medical image that corresponds to the sight line information $E_t$, the display condition $O_{tl}/O_{tw}$, the display luminance $O_{tb}$, and the CT value $O_{th}$. When sight line information is NULL, these values also become NULL. Since the display luminance is obtained from the display condition and the CT value, it can also be omitted from the observation region information.

In step S200, the image obtaining unit 41 reads out a medical image from the database 22 via the communication IF 31 and the LAN 21, and provides it to the display processing unit 42. The display processing unit 42 displays the medical image on the display unit 36. The user starts radiogram interpretation of the medical image displayed on the display unit 36 by using the function of a well-known image display system.

In step S201, the sight line obtaining unit 43 obtains sight line information of the user during radiogram interpretation via the sight line detection unit 37. For example, $E_1(710, 550)$ is obtained at every 0.1 sec as sight line information. In step S202, the condition obtaining unit 44 obtains the display condition of the medical image displayed on the display unit 36. For example, WL −600/WW 1500 is obtained as the display condition. Further, in step S203, the recording unit 45 records observation region information $O_t$ corresponding to the sight line information by using the sight line information obtained in step S201 and the display condition obtained in step S202. In this embodiment, the observation region information is obtained at every 0.1 sec in time series and recorded.

Figure 3:
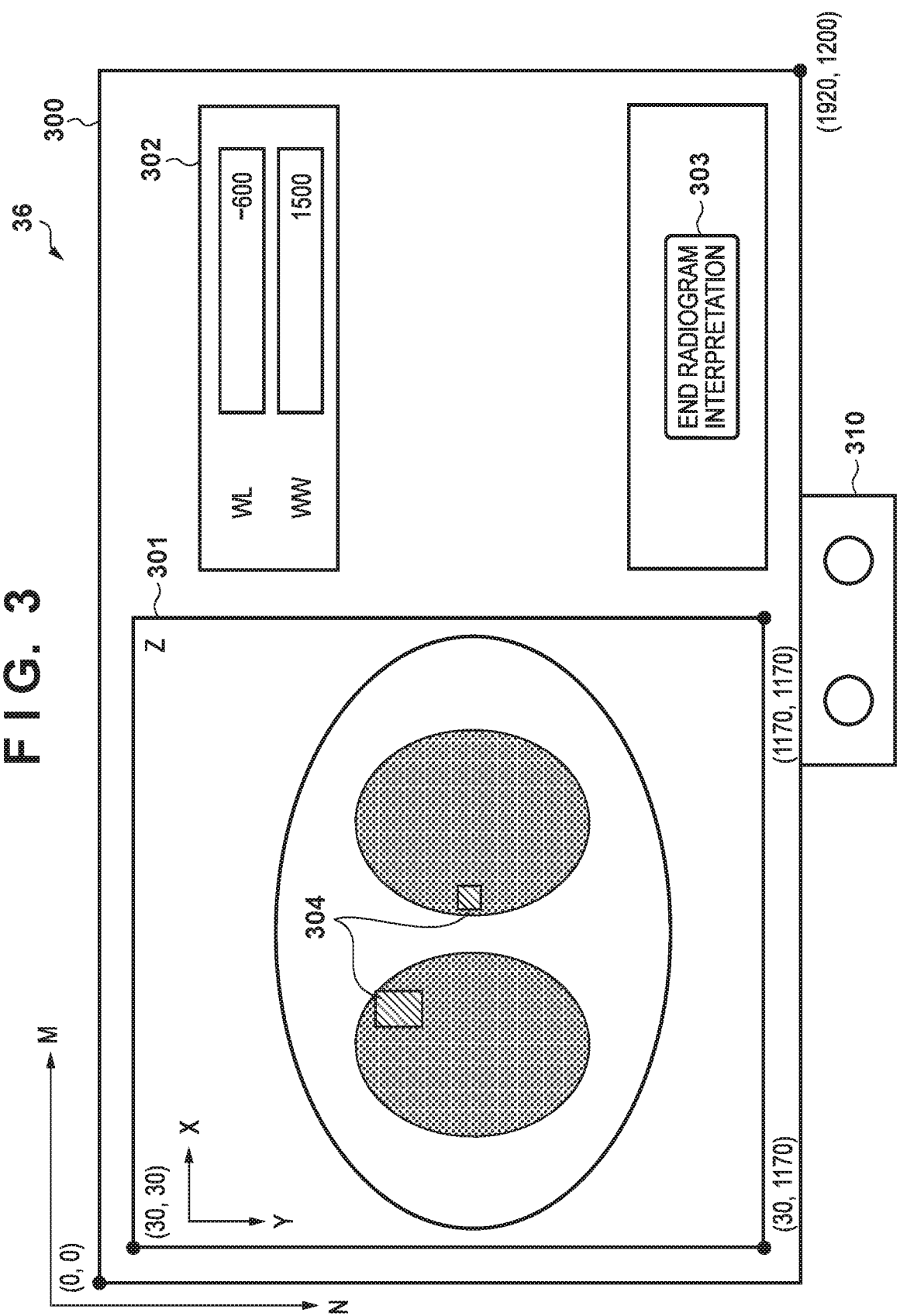
FIG. 3 is a view showing an example of a screen according to the first embodiment.

For example, a case in which the display condition is WL −600/WW 1500, the luminance of $E_1(710, 550)$ on the display unit 36 is 25, Pos corresponding to this pixel is (100, 150, 140), and the CT value is −1200 will be examined. In this case, $O_{1p}(100, 150, 140)$, $O_{1w}=1500$, $O_{1l}=-600$, $O_{1b}=25$, and $O_{1h}=-1200$ are stored as observation region information $O_1$. Note that the coordinate value of the voxel Pos corresponding to the pixel indicated by the sight line information is obtained by, for example, converting the coordinate value (sight line information) (M, N) of the pixel on the display screen as shown in FIG. 3 into an (X, Y, Z) coordinate value in the medical image during display. Since the position of a display area 301 for displaying a tomographic image on a screen 300 of the medical image is known and the Z-coordinate of a displayed tomographic image is known, the coordinate value of the voxel Pos corresponding to the sight line information can be obtained from these parameters.

In step S204, the determination unit 46 determines, from an input from the user via the operation unit 35, whether radiogram interpretation has ended. Note that determination of whether radiogram interpretation has ended is performed at a specific sampling rate. If the determination unit 46 determines that radiogram interpretation has not ended (that is, there is no input from the user), the processes in steps S201 to S203 are repeated. If the determination unit 46 determines that radiogram interpretation has ended, the process advances to step S205. Note that an input from the user is entered by, for example, clicking a button 303 for designating the end of radiogram interpretation, as shown in FIG. 3.

In steps S205 and S206, the marker generation unit 47 and the display processing unit 42 perform identification display so that the user can identify a region determined to have been observed or another region. First, in step S205, the marker generation unit 47 generates a marker to be displayed on the image by using the observation region information obtained in step S203. In this embodiment, the display luminance is obtained as state information representing the display state of the medical image at the detected gaze position. Based on this state information, it is determined whether a region in the medical image that corresponds to the gaze position has been observed. In this embodiment, a marker is generated at a portion (unobserved region) not identified as an observed region. The observed region is the region of a pixel in which the display luminance is 1 to 254 and the sight line has been detected even once. That is, a region (voxel position $O_{tp}$ obtained from sight line information) that has the display luminance $O_{tb}$ of 1 to 254 and has been observed at least once in the observation region information $O_t$ (t=1, 2, . . . ) is identified as an observed region. In other words, even if the sight line is detected in a region having a display luminance of 0 or 255, this region is not determined to have been observed. This is because it is only known that a region having the display luminance of 0 or 255 falls outside a CT value range defined by the display condition, and even if CT values are different, the contrast is not different, and the difference between the CT values cannot be recognized. The marker is implemented by superposing and displaying a layer in which a pixel corresponding to an unobserved region is colored in red.

Figure 4:
FIG. 4 is a table for explaining an identification condition according to the first embodiment.

Determination of an observed region by the marker generation unit 47 will be explained in detail with reference to the table of FIG. 4. In this example, radiogram interpretation is performed under the mediastinal condition (WL 35/WW 350) in $O_1$ to $O_5$, and under the lung field condition (WL −600/WW 1500) in $O_8$ and $O_9$. In $O_1$ (and $O_2$), the display luminance $O_{tb}$ is 138 and falls within the range of 1 to 254, and the marker generation unit 47 identifies (200, 250, 150) indicated by $O_{1p}$ and $O_{2p}$ as an observed region. Since the display luminance is 0 in $O_3$ to $O_5$, the marker generation unit 47 does not identify $O_{3p}$(200, 230, 150), $O_{4p}$(210, 230, 150), and $O_{5p}$(220, 200, 150) as observed regions even if sight line information is detected. Although $O_8$ (and $O_9$) has the same Pos (and CT value) as that (those) of $O_5$, the luminance falls within the range of 1 to 254 in accordance with the display condition, and the marker generation unit 47 identifies $O_{8p}$(220, 200, 150) as an observed region. In this manner, even if the same position is observed, the position may or may not be identified as "observed" depending on the display condition.

In step S206, the display processing unit 42 displays, on the display unit 36, the medical image obtained in step S200 and the marker generated in step S205. FIG. 3 shows an example of part of the apparatus arrangement according to this embodiment, and an example of a screen in which a generated layer is superposed and displayed on a medical image. The screen 300 is an example of the screen of the display unit 36, and the axial tomographic image of a three-dimensional medical image is displayed in the display area 301 by a well-known image display system. The screen 300 has a condition input area 302, and the button 303 for designating the end of radiogram interpretation. The user can perform radiogram interpretation under an arbitrary display condition by changing the WL value and WW value of the condition input area 302 during radiogram interpretation. Markers 304 are generated by the marker generation unit, and indicate regions (that is, unobserved regions) not identified as observed regions. An eye tracker 310 is an example of the sight line detection unit 37, is arranged below the screen 300, and obtains a gaze position (sight line information) on the screen 300.

As described above, in the image diagnosis assistance apparatus 10 according to the first embodiment, even if the sight line is detected at a portion for which it is determined that radiogram interpretation cannot be properly performed because the CT value falls outside the range of the display condition and the luminance becomes the same, this portion is not identified as an observed region. Further, a region not identified as "observed" can be visualized using a marker. Hence, the influence of the display condition on radiogram interpretation by the doctor is taken into account, and a high-quality radiogram interpretation omission preventing technique can be provided.

(Modification 1-1)

In the first embodiment described above, information representing a pixel (one pixel) looked on the display unit 36 is used as sight line information. However, the sight line information may not always be one pixel. For example, a plurality of pixels at a predetermined distance (for example, close by eight or four) from a pixel at which the sight line has been detected may be used as sight line information in consideration of the field of view of a human. Expansion of pixels will be described in more detail with reference to FIG. 11.

(Modification 1-2)

In the first embodiment, in step S205, (1) that the display luminance is proper (for example, falls within a range of 1 to 244), and (2) that the gaze position has been detected even once in a region (pixel) are used as conditions to determine by the marker generation unit 47 that the region (pixel) has been observed. However, the determination condition is not limited to them. For example, as condition (1), another luminance value range (for example, 50 to 200) other than 1 to 244 may be used. As for condition (2), for example, a region observed accumulatively for 3 sec or more may be identified as an observed region. For example, when the sampling rate is 0.1 sec, such a region is equivalent to a region (pixel) where the gaze position has been detected 30 times or more. Alternatively, a region observed continuously for 1 sec or more may be identified as an observed region in consideration of the residence time of the sight line. Note that the numerical values cited here are merely examples for the explanation, and the present invention is not limited to these numerical values.

(Modification 1-3)

According to the first embodiment, in step S205, the marker generation unit 47 generates a marker to superpose and display it by a layer in which a corresponding pixel is colored in red, so that an unobserved region can be identified from another region. However, the form of the marker is not limited to this. For example, a figure such as a triangle or rectangle may be superposed and displayed, or the color may be reversed. When a figure is superposed and displayed, for example, it is only necessary to make the barycenter of the figure to be displayed and the barycenter of an unobserved region coincide with each other and display the figure. As a matter of course, the present invention is not limited to these examples, and any display method may be employed as long as an unobserved region can be discriminated from another region.

Second Embodiment

In the first embodiment, it is considered that proper radiogram interpretation cannot be performed in a region having a display luminance of 0 or 255. Even if sight line information is detected in such a region, this region is not identified as "observed". However, proper radiogram interpretation cannot be performed not only when the display luminance is 0 or 255. For example, a normal liver takes a CT value of about 60 to 70, and a fatty liver takes a CT value of 20 to 40. Depending on the display condition, however, the luminance becomes almost the same for the CT values of 20 to 70. In this case, no satisfactory contrast difference is obtained in regard to the display of the liver, and it is difficult to identify a normal liver and a fatty liver. Even if radiogram interpretation is performed in this state, proper radiogram interpretation is hard.

To solve this, an image diagnosis assistance apparatus according to the second embodiment identifies an observed region in consideration of whether a predetermined CT value range can be identified under the display condition. More specifically, in the first embodiment, the display luminance is used as the display state of the display screen that is decided based on the display condition. However, in the second embodiment, it is determined based on the display condition whether a predetermined CT value range is displayed with a proper contrast on the display screen. Note that the predetermined CT value range is decided based on importance in radiogram interpretation. For example, the predetermined CT value range is set based on the possible CT value range of an important organ or tissue in radiogram interpretation. Hence, the CT value range may be changed in accordance with the imaging portion of a medical image to be interpreted. Note that the arrangement of an image diagnosis assistance apparatus 10 according to the second embodiment is the same as that in the first embodiment (FIG. 1). Assume that each functional component in a control unit 38 is implemented by software, as in the first embodiment.

The processing sequence of the image diagnosis assistance apparatus 10 according to the second embodiment will be explained with reference to the flowchart of FIG. 2. Note that the first and second embodiments are different especially in part of processing in step S205. Therefore, processes in steps S200 to S204 and S206 are the same as those described in the first embodiment.

In step S205, a marker generation unit 47 generates a marker to be displayed on an image by using observation region information obtained in step S203. Also in the second embodiment, a marker is generated at a portion (unobserved region) not identified as an observed region. In the second embodiment, however, whether the target region is an observed region is decided from the predetermined CT value range and the display condition. The marker is implemented by superposing and displaying a layer in which a pixel corresponding to an unobserved voxel is colored in red, as in the first embodiment.

Figures 5A, 5B, 5C:
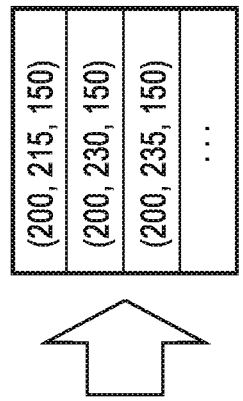
FIGS. 5A to 5C are tables for explaining an identification condition according to the second embodiment.

In the second embodiment, the entire range of pixel values used in an imaging apparatus that captured a medical image is divided in advance into a plurality of partial ranges. Whether the gaze position has been observed is determined based on the size of the range of display luminance values when the partial range of pixel values to which a pixel value corresponding to the gaze position belongs is displayed on the display screen. For example, in the case of a CT apparatus having an entire pixel value range of −2048 to 2047, a CT value range ($W_j$, j=1 to 7) as shown in FIG. 5A is defined as the partial range. In FIG. 5A, $R_j$ represents the range of possible CT values of $W_j$. In this embodiment, based on the ratio of a partial range to which a pixel value corresponding to a gaze position belongs, and a range used for display on the display screen out of the entire range of pixel values used in an apparatus that captured a medical image, the marker generation unit 47 determines whether the gaze position has been observed. More specifically, when the width of the CT value range $W_j$ to which the CT value $O_{th}$ of observation region information $O_t$ belongs is equal to or larger than ⅛ of WW, the marker generation unit 47 identifies, as an observed region, a voxel position $O_{tp}$ indicated by the observation region information $O_t$. This is because, if the range of possible CT values of a portion or tissue to undergo radiogram interpretation is much narrower than WW, the contrast difference at the target portion or tissue is almost lost on the display screen, and proper radiogram interpretation cannot be performed, as described above. As in the first embodiment, a region having a luminance of 0 or 255 is excluded from an observed region.

The processing in step S205 will be explained in detail with reference to FIG. 5B. In this example, radiogram interpretation is performed under the lung field condition (WL −600/WW 1500) in $O_1$ to $O_4$, and under the mediastinal condition (WL 35/WW 350) in $O_7$ to $O_9$. Since the CT values in $O_1$ to $O_3$ are $O_{1h}$=70, $O_{2h}$=90, and $O_{3h}$=55, it is known from FIG. 5A that these CT values belong to $W_5$. The width of $W_5$ is 50, which is smaller than ⅛ (=187.5) of WW 1500 of the display condition in $O_1$ to $O_3$, so $O_{1p}$ to $O_{3p}$ are not identified as observed regions regardless of the display luminance. The CT value ($O_{4h}$=−650) in $O_4$ belongs to $W_2$, the width "900" of $W_2$ is equal to or larger than ⅛ of WW 1500, the luminance falls within the range of 1 to 254, so $O_{4p}$(200, 215, 150) is identified as an observed region.

Parameters in $O_7$ are the same as those in $O_4$ except the display condition, but the display luminance is 0, and thus $O_7$ is not identified as an observed region. However, since (200, 215, 150) is identified as an observed region in $O_4$, (200, 215, 150) is the observed region as a whole. Parameters in $O_8$ and $O_9$ are the same as those in $O_3$ and $O_2$ except the display condition, but the width "50" of $W_5$ to which CT values belong are equal to or larger than ⅛ (=43.75) of WW 350 of the display condition, and luminances also fall within the range of 1 to 254. Therefore, $O_{8p}$(200, 235, 150) and $O_{9p}$(200, 240, 150) are identified as observed regions. In this fashion, observed regions as shown in FIG. 5C are obtained.

As described above, in the image diagnosis assistance apparatus 10 according to the second embodiment, even if the sight line is detected in a region for which it can be determined that radiogram interpretation cannot be properly performed as a result of tone conversion in the range of possible CT values of a specific portion or tissue in accordance with the display condition, the region is not identified as an observed region. That is, the marker generation unit 47 determines that a radiogram interpretation target portion at which the luminance contrast difference becomes small on the display screen is a region where radiogram interpretation cannot be properly performed. The marker generation unit 47 handles this portion as an unobserved region, and generates a marker for visualizing this result. Therefore, a high-quality radiogram interpretation omission preventing technique can be provided.

(Modification 2-1)

In the second embodiment, an observed region is identified from the relationship with the display condition by using a predetermined CT value range in step S205. However, the CT value range may be set dynamically. For example, the CT value range may be decided dynamically from the display condition, or the user may set a CT value range.

Third Embodiment

In the first and second embodiments, whether the display state is suited to radiogram interpretation is determined based on the display condition and the luminance value. When it is determined that the display state is not suited to radiogram interpretation, even if the sight line is detected, this region is not identified as an observed region. However, it is often the case that the CT value becomes high and the luminance becomes 255 even in a region to which the doctor need not pay so much attention, like metal. Thus, such a region is not identified as an observed region. In an image diagnosis assistance apparatus 10 according to the third embodiment, a region to which the doctor need not pay attention is identified as an observed region regardless of the display condition. Since a region to which the doctor need not pay attention is classified as an observed region regardless of sight line information or the display state, the need to pay doctor's attention to an unnecessary region can be obviated.

The arrangement of the image diagnosis assistance apparatus 10 according to the third embodiment is the same as that in the first embodiment (FIG. 1). Assume that each functional component of a control unit 38 is implemented by software, as in the first embodiment. Processing according to the third embodiment will be explained with reference to the flowchart of FIG. 2. Note that processes in steps S200 to S204 and S206 are the same as those described in the first embodiment. The third embodiment is different from the first embodiment in part of processing in step S205, and the processing in step S205 will be explained below.

In step S205, a marker generation unit 47 generates a marker to be displayed on an image by using observation region information obtained in step S203. Also in the third embodiment, a marker is generated in a region (unobserved region) not identified as an observed region. First, based on the CT value of a medical image, the marker generation unit 47 identifies, as an observed region, all voxels each having a CT value falling outside a predetermined CT value range. For example, it suffices to use the CT value of an air portion (−1000) or a metal portion (4000) to which the doctor need not pay attention. In the third embodiment, all voxels each having a CT value range other than −1000 to +4000 are identified as an observed region. After that, the same processing as those in the first and second embodiments is performed, and it is identified whether a portion not identified as an observed region has been observed.

As described above, in the image diagnosis assistance apparatus according to the third embodiment, a region to which the doctor need not pay attention, like a metal or the air portion, does not influence proper radiogram interpretation and is identified as an observed region in advance. In other words, a region that does not influence proper radiogram interpretation can be identified as an observed region regardless of detection/non-detection of sight line information or the display condition. As a result, more efficient, high-quality radiogram interpretation omission prevention can be provided.

(Modification 3-1)

In the third embodiment, all voxels each having a CT value falling outside the predetermined CT value range (−1000 to +4000) are identified as an observed region based on the predetermined CT value range in step S205 regardless of whether sight line information has been detected. However, the above-described method may be applied to a region where sight line information has been detected. That is, the marker generation unit 47 identifies, as an observed region, even a voxel having a CT value falling outside the predetermined CT value range even if the voxel belongs to a region not identified as an observed region though sight line information has been detected. According to this method, a region where the sight line has not been detected is identified not as "observed" even when the region has a CT value falling outside the predetermined CT value range. A higher-quality radiogram interpretation omission preventing technique can be provided.

(Modification 3-2)

In the third embodiment, the CT value range is determined based on a clinically meaningless CT value in step S205. However, the CT value range is not limited to such a value. For example, all CT values falling outside the display condition range may be identified as an observed region based on the display condition. The user may also set an arbitrary CT value range.

(Modification 3-3)

In the third embodiment, a region to which the doctor need not pay attention is determined based on the CT value range in step S205, and all regions to which it is determined that no attention need be paid are identified as observed regions. However, the present invention is not limited to the method using the CT value range. For example, the control unit 38 may analyze a medical image to detect the body surface of an object, determine that a region outside the body surface is a region to which the doctor need not pay attention, and identify all regions outside the body surface as observed regions.

In the first to third embodiments, the correspondence between the pixel value range defined by the display condition, and the display luminance is linearly defined, as represented by conditional expression (1), but is not limited to this. The pixel value range defined by the display condition may be nonlinearly associated with the display luminance. Although the display luminance $O_{tb}$ is obtained based on the display condition, it may be directly obtained from display data to the display unit 36. The voxel position $O_p$ in a three-dimensional medical image is held as observation region information. However, if the result of identifying whether a region has been observed need not be expanded to a three-dimensional medical image, a pixel position in a tomographic image may be held. Note that an image diagnosis assistance apparatus that identifies, as "observed", a voxel position of a three-dimensional medical image that corresponds to an observed pixel position in a tomographic image will be explained in detail in the fourth and subsequent embodiments below.

Fourth Embodiment

The first to third embodiments have described an example in which a tomographic image in a single tomographic direction is interpreted. However, in radiogram interpretation of a three-dimensional medical image, radiogram interpretation is frequently performed using a plurality of tomographic images generated in different tomographic directions. A general image diagnosis assistance apparatus as described in literature 1 does not have a concept that sight line information detected in a tomographic image in a given tomographic direction is associated with a position in a tomographic image in another tomographic direction. As a result, even a region identified as an observed region in a tomographic image in a given tomographic direction is identified as an unobserved region in a tomographic image in another tomographic direction. In addition, there is a need of the radiogram interpreter to observe a specific region in a plurality of tomographic directions. However, in literature 1, it is not taken into account whether the same region has been observed in a plurality of tomographic directions, so it cannot be identified whether the region has been observed properly.

In the fourth and subsequent embodiments, a pixel observed in a tomographic image generated from a three-dimensional medical image is detected based on a gaze position $E_t$, and the observed pixel is expanded to a voxel $O_p$ of the three-dimensional medical image. Accordingly, radiogram interpretation omission can be efficiently prevented using sight line information obtained in a tomographic image obtained from a three-dimensional medical image.

An image diagnosis assistance apparatus 10 according to the fourth embodiment obtains medical information (for example, information of a medical image or electronic medical chart) regarding the case of a diagnosis target, and input information from a user (for example, sight line information of a user or operation information of a GUI), and performs diagnosis assistance regarding this case. This embodiment will be explained using an example in which tomographic images of a chest X-ray CT image in a plurality of tomographic directions are handled as an example of a three-dimensional medical image. More specifically, a tomographic image in an axial plane (to be referred to as an axial tomographic image hereinafter) perpendicular to the body axis direction parallel to the top and bottom (caput and cauda) of the body, a tomographic image in a coronal plane (to be referred to as a coronal tomographic image hereinafter) perpendicular to the coronal direction parallel to the front and back (abdomen and back) of the body, and a tomographic image in a sagittal plane (to be referred to as a sagittal tomographic image hereinafter) perpendicular to the sagittal direction parallel to the left and right of the body are used. Needless to say, the assistance targets are not limited to them, and any of the following embodiments is merely an example for explaining processing of the image diagnosis assistance apparatus 10.

In the fourth embodiment, when a given region is observed, this region is identified as "observed" in an entire three-dimensional medical image regardless of a tomographic image in which the region has been observed. For example, when a given region is observed in an axial tomographic image, even if corresponding regions are not observed in a coronal tomographic image and a sagittal tomographic image, this region is identified as "observed" in a three-dimensional medical image.

The arrangement of the image diagnosis assistance apparatus 10 according to the fourth embodiment, and the functional arrangement of a control unit 38 are the same as those in the first embodiment (FIG. 1). Note that a condition obtaining unit 44 can be omitted in the control unit 38. By using sight line information obtained by a sight line obtaining unit 43, a recording unit 45 obtains data corresponding to the sight line information as observation region information. This information is recorded as time-series information. Based on the identification condition and the generation condition, a marker generation unit 47 generates a marker to be displayed on an image by using the observation region information recorded as the time-series information by the recording unit 45, and outputs the marker to a display processing unit 42. Note that the identification condition is a condition for identifying an observed region or an unobserved region, and the generation condition is a condition for generating a marker, details of which will be described later.

Figure 6:
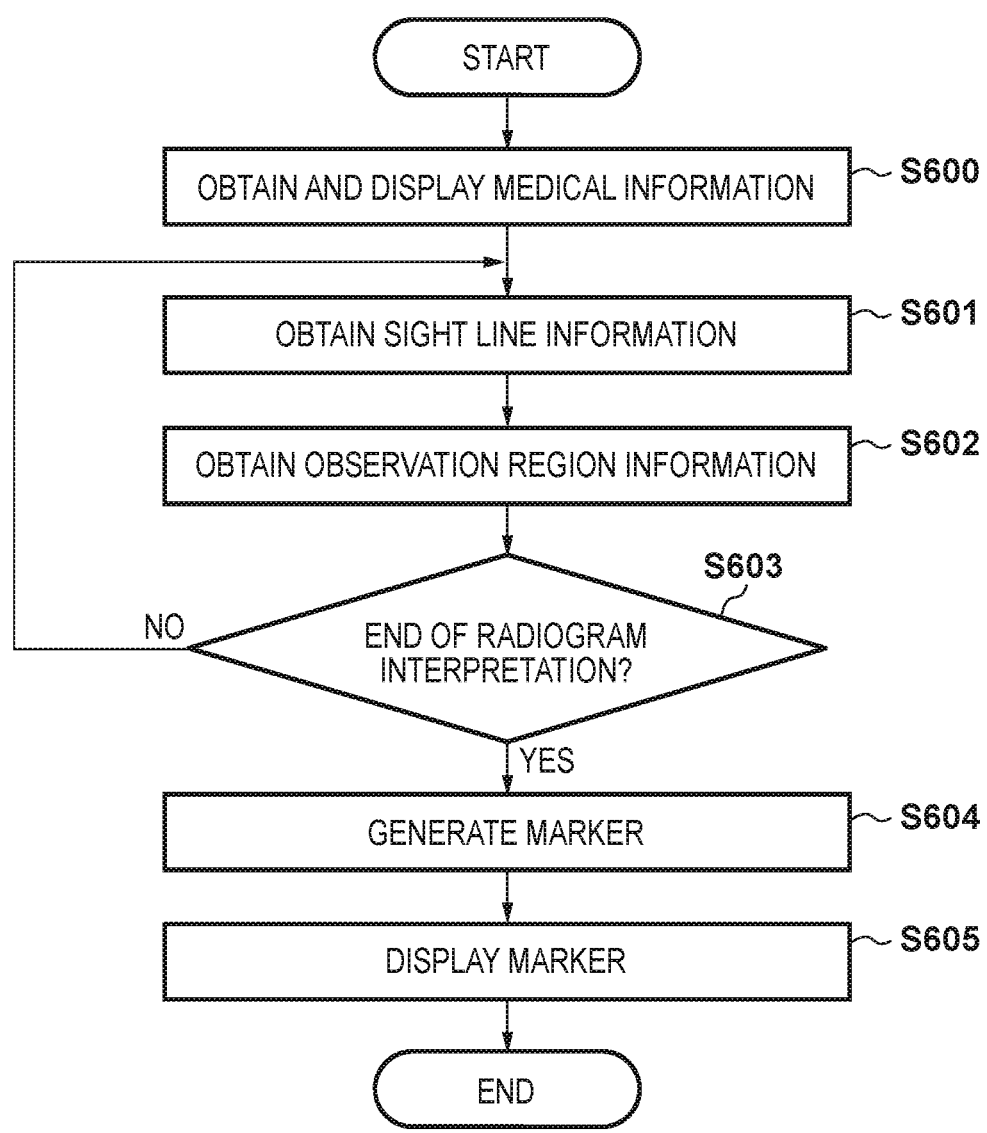
FIG. 6 is a flowchart for explaining overall processing according to the fourth to seventh embodiments.

Next, processing to be performed by the control unit 38 according to the fourth embodiment will be explained with reference to the flowchart of FIG. 6. In the following description, the positions of the pixels of a display unit 36 are represented in an M-N coordinate system, and the positions of the voxels of a three-dimensional medical image are represented in an X-Y-Z coordinate system. The position of one pixel of the display unit 36 is represented by the (m, n) coordinate form, and the position of one voxel of a three-dimensional medical image is represented by the (x, y, z) coordinate form. Assume that m, n, x, y, and z represent the position of one pixel or one voxel and take integer values. As in the above-described embodiments, a CT value is stored as signed 16 bits in each voxel of a three-dimensional medical image, and the CT value stored in the voxel is converted into a luminance (display luminance) and displayed on the display unit 36.

Figure 7:
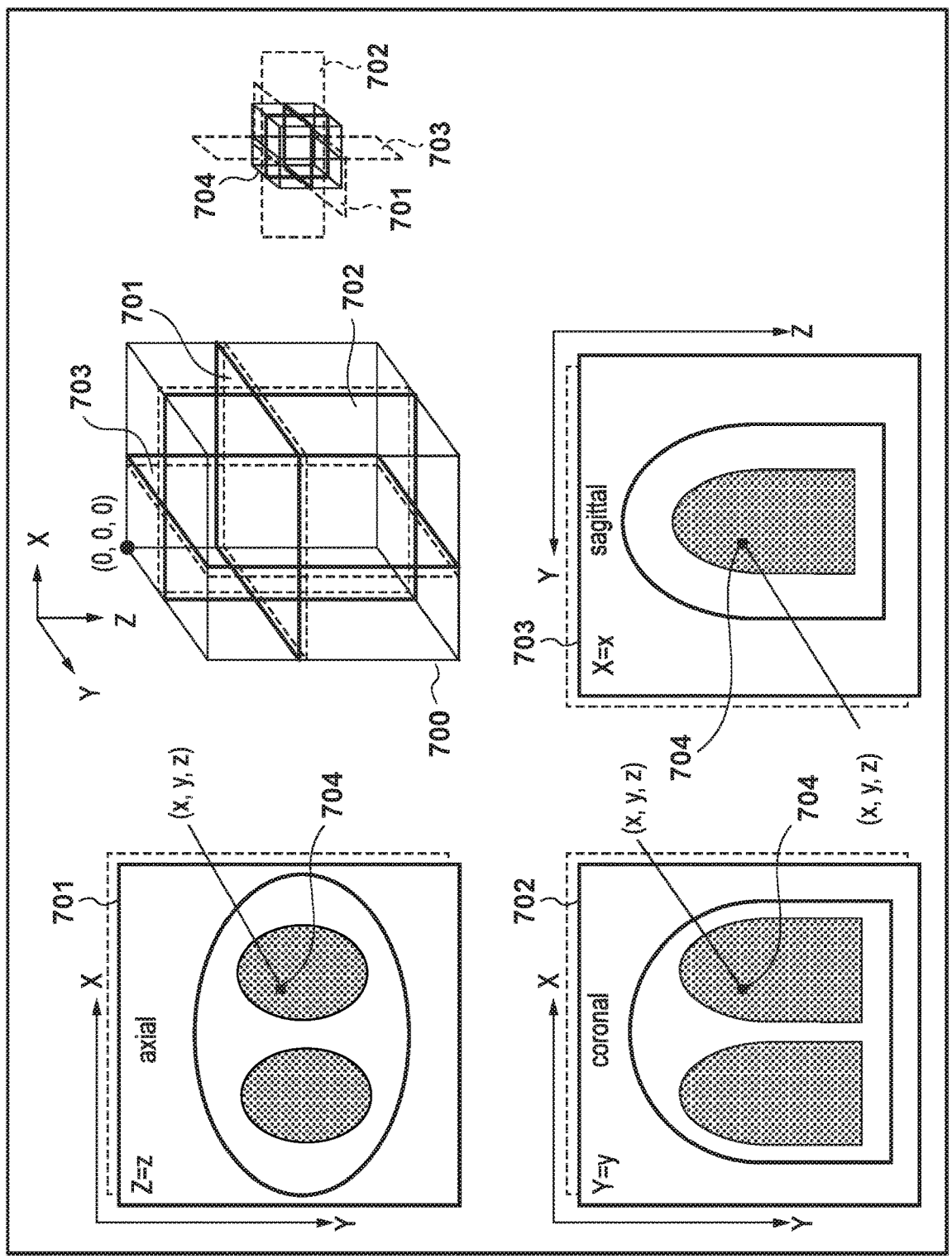
FIG. 7 is a view showing an axial tomographic image, a coronal tomographic image, and a sagittal tomographic image.

FIG. 7 shows an example in which a three-dimensional medical image is represented by an axial tomographic image, a coronal tomographic image, and a sagittal tomographic image. When an X-Y-Z coordinate system as shown in FIG. 7 is set with respect to a three-dimensional medical image 700, the respective tomographic images are indicated by planes perpendicular to each other. In general, an axial tomographic image 701 is represented by an X-Y plane at a given Z-coordinate, a coronal tomographic image 702 is represented by an X-Z plane at a given Y-coordinate, and a sagittal tomographic image 703 is represented by a Y-Z plane at a given X-coordinate. When a position is designated in an arbitrary tomographic image, a position in the three-dimensional medical image 700 is determined. For example, when one pixel in a tomographic image corresponds to one voxel, if one point is designated as a point 704 of interest in the axial tomographic image 701 having a Z-coordinate of z, X- and Y-coordinates are decided, and the voxel (x, y, z) is uniquely determined. Therefore, as shown in FIG. 7, the point 704 of interest can be displayed even in the coronal tomographic image 702 having a Y-coordinate of y and the sagittal tomographic image 703 having an X-coordinate of x. This embodiment will be explained using an example in which one pixel of a tomographic image corresponds to one voxel of a three-dimensional medical image.

Assume that detection of sight line information by a sight line detection unit 37 is performed at a predetermined sampling rate (for example, 0.1 sec), and sight line information at a given time point t is represented by $E_t(e_{tm}, e_{tn})$ (t=1, 2, ...), as in the first to third embodiments. $e_{tm}$ represents an M-coordinate on the display unit 36, and $e_{tn}$ represents an N-coordinate on the display unit 36. When a position where the sight line has been detected is outside the display unit 36, sight line information becomes NULL.

Figure 8:
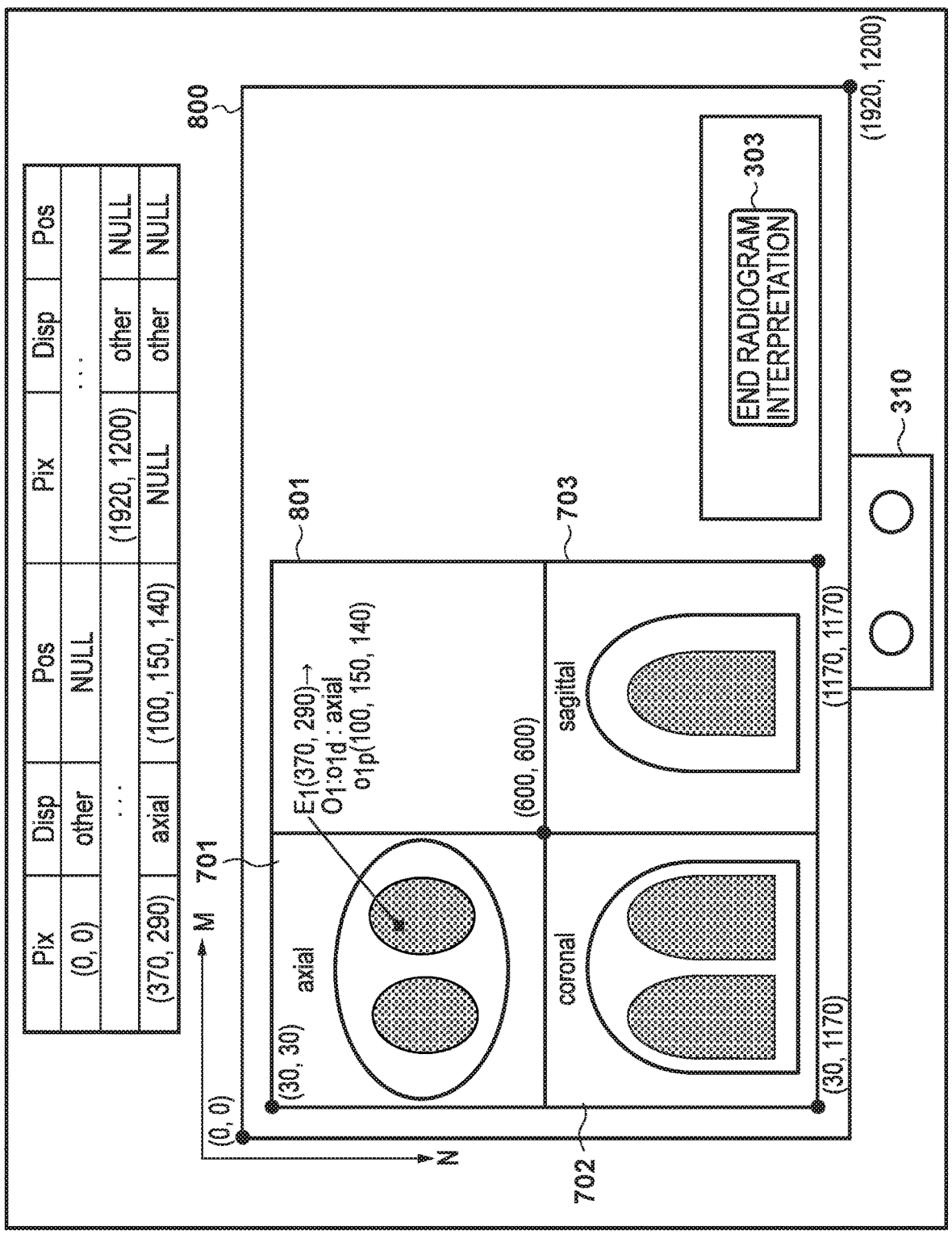
FIG. 8 is a view showing an example of observation region information.

FIG. 8 shows the relationship between the display form of a screen 800 of the display unit 36, and sight line information using M- and N-coordinates when the upper left corner of the screen 800 is defined as an origin. $O_t$ represents observation region information at $E_t$. Assume that $O_t$ has "information (display content Disp) representing a content displayed in a region (pixel) of the display unit 36 that is indicated by sight line information", and "information (position information Pos) representing a displayed region (voxel) of a three-dimensional medical image". In the following description, $O_{td}$ represents the display content Disp corresponding to the observation region information $O_t$ at time t, and $O_{tp}$ represents position information Pos. $O_{td}$ has, as its display content, the type of a tomographic image, that is, one of "axial", "coronal", "sagittal", and "other". $O_{tp}$ indicates the position of a voxel by the (x, y, z) coordinate form. When $O_{td}$ is "other" or there is no corresponding voxel in a three-dimensional medical image (for example, a region outside data), $O_{tp}$ becomes NULL.

In step S600, an image obtaining unit 41 of the image diagnosis assistance apparatus 10 reads out a medical image from a database 22 via a communication IF 31 and a LAN 21, and provides it to a display processing unit 42. The display processing unit 42 displays the medical image on the display unit 36. The user starts radiogram interpretation of the medical image displayed on the display unit 36 by using the function of a well-known image display system. In step S601, the sight line obtaining unit 43 obtains sight line information of the user during radiogram interpretation via the sight line detection unit 37. For example, assume that $E_1(370, 290)$ is obtained. Then, in step S602, the recording unit 45 records observation region information corresponding to the sight line information in, for example, a storage unit 34 by using the sight line information obtained in step S601.

The observation region information represents information (display content Disp) representing a content displayed in a pixel (to be referred to as Pix) corresponding to a gaze position on the display unit 36 at a given time point (t=1), and information (position information Pos) representing a displayed voxel of a three-dimensional medical image. In the example of FIG. 8, m is an M-coordinate, and n is an N-coordinate. In the case of 30<m<600 and 30<n<600, the display content Disp is "axial". In the case of 30<m<600 and 600<n<1170, the display content Disp is "coronal". In the case of 600<m<1170 and 600<n<1170, the display content Disp is "sagittal". For other coordinate values, the display content Disp is "other".

Further, FIG. 8 shows an example of sight line information $E_1$ and corresponding observation region information $O_1$. In this example, a pixel indicated by sight line information $E_1$ (370, 290) is associated with "axial" as the display content Disp, and (100, 150, 140) as the position information Pos. In the example of FIG. 8, therefore, $O_{1d}$: axial and $O_{1p}$: (100, 150, 140) are obtained as the observation region information $O_1$ corresponding to the sight line information $E_1$.

In step S603, a determination unit 46 determines, from an input from the user via an operation unit 35, whether radiogram interpretation has ended. Note that determination of whether radiogram interpretation has ended is performed at a specific sampling rate. If the determination unit 46 determines that radiogram interpretation has not ended (that is, the user has not input designation of the end), the processes in steps S601 and S602 are repeated. If the determination unit 46 determines that radiogram interpretation has ended, the process advances to step S604. Note that an input from the user is entered by, for example, clicking a button 303 for designating the end of radiogram interpretation.

In steps S604 and S605, the marker generation unit 47 and the display processing unit 42 perform identification display so that the user can identify a region identified as "observed" or another region in a three-dimensional medical image. In step S604, based on the identification condition and the generation condition, the marker generation unit 47 generates a marker to be displayed on the image by using the observation region information obtained in step S602. The identification condition is a condition for determining whether a region determined to have been observed in a tomographic image is identified as an observed region in a three-dimensional medical image. The generation condition designates whether to identifiably display an observed region or to identifiably display an unobserved region. In this embodiment, the identification condition is "$O_{tp}$ that has appeared once or more is identified as an observed voxel regardless of $O_{td}$ in the observation region information $O_t$". That is, a voxel that has appeared even once in observation region information is identified as an observed region, and another voxel is identified as an unobserved region regardless of the tomographic direction of a tomographic image. The marker generation condition is "a voxel identified as an unobserved region is targeted". Further, the marker is superposed and displayed on a corresponding voxel by a layer in which a pixel at a corresponding portion in each tomographic image is colored in red.

For simplicity, a case in which a three-dimensional medical image is formed from 2×2×2=8 voxels will be explained with reference to FIGS. 9A to 9D. Assume that pieces of observation region information $O_1$ to $O_{20}$ as shown in FIG. 9D are obtained. In this case, voxels observed once or more in an axial tomographic image are five voxels of (1, 2, 1), (1, 2, 2), (2, 1, 1), (2, 2, 1), and (2, 2, 2). Similarly, voxels observed once or more in a coronal tomographic image are three voxels of (1, 2, 2), (2, 1, 1), and (2, 2, 2), and voxels observed once or more in a sagittal tomographic image are four voxels of (1, 1, 2), (2, 1, 1), (2, 1, 2), and (2, 2, 2). In FIG. 9A, a voxel observed once or more in each tomographic image is grayed. By ORing these voxels, observed regions can be identified. In the example of FIGS. 9A to 9C, seven voxels of (1, 1, 2), (1, 2, 1), (1, 2, 2), (2, 1, 1), (2, 1, 2), (2, 2, 1), and (2, 2, 2) are identified as observed regions, and a voxel of (1, 1, 1) is identified as an unobserved region (FIG. 9B). As shown in FIG. 9C, the marker generation unit 47 generates layers (markers) in which portions of the voxel identified as an unobserved region that correspond to the axial tomographic image, coronal tomographic image, and sagittal tomographic image are colored in red.

In step S605, the display processing unit 42 displays, on the display unit 36, the medical image obtained in step S600 and the markers generated in step S604. Note that the marker that is generated by the marker generation unit 47 can be variously modified, as described in modification 1-3.

FIG. 10 shows an example of a screen in which a generated layer (marker) is superposed and displayed on a medical image. On the screen 800 of the display unit 36, the axial tomographic image 701, coronal tomographic image 702, and sagittal tomographic image 703 of the three-dimensional medical image 700 (FIG. 7) are displayed in an image display area 801 by a well-known image display system. Layers (markers) 1001 generated by the marker generation unit 47 are superposed and displayed on the axial tomographic image 701, the coronal tomographic image 702, and the sagittal tomographic image 703, respectively.

As described above, in the image diagnosis assistance apparatus 10 according to the fourth embodiment, a given region can be identified as an observed region in a three-dimensional medical image regardless of a tomographic image in which the region has been observed, and information can be visualized and displayed based on the observed region. That is, a region that has already been observed in a given tomographic image is not identified as an unobserved region in another tomographic image, so radiogram interpretation omission can be prevented efficiently. It is also apparent that determination of an observed region in each tomographic image may use determination considering a display condition as described in the first to third embodiments.

(Modification 4-1)

In the fourth embodiment, in step S602, the position information $O_{tp}$ in the observation region information $O_t$ represents a voxel of a three-dimensional medical image that corresponds to a pixel represented by the sight line information $E_t$. That is, $O_{tp}$ represents one voxel corresponding to the sight line information, but need not always represent only a voxel in one-to-one correspondence with a pixel. For example, in consideration of the field of view of a human, $O_{tp}$ may represent a plurality of voxels corresponding to pixels within a predetermined distance from a pixel represented by $E_t$ in a tomographic image in which the sight line information $E_t$ has been detected.

FIG. 11 shows an example of the positions $O_{tp}$ of a plurality of observed voxels when a voxel corresponding to the sight line information $E_t$ is indicated by (x, y, z) and a predetermined distance D=1. First, the case of an axial tomographic image will be examined. Since the axial tomographic image is represented by an X-Y plane, Z is the same within the plane. When pixels (for example, four pixels adjacent to the top, bottom, left, and right of a gaze point) within the distance D from the gaze point (sight line information $E_t$) are obtained within the plane (axial tomographic image) in consideration of the field of view, voxels corresponding to these pixels have the same Z value. Similarly, since a coronal tomographic image is represented by an X-Z plane, corresponding voxels have the same Y value. Since a sagittal tomographic image is represented by a Y-Z plane, corresponding voxels have the same X value. Therefore, even if a voxel corresponding to the sight line information $E_t$ is the same (for example, (x, y, z)), the positions $O_{tp}$ of a plurality of observed voxels obtained from the axial tomographic image, the coronal tomographic image, and the sagittal tomographic image are different. In the example of FIG. 11, when the sight line information $E_t$ is detected in the axial tomographic image, five voxels of (x, y, z) and surrounding (x−1, y, z), (x+1, y, z), (x, y−1, z), and (x, y+1, z) are obtained as $O_{tp}$. Similarly, when the sight line information $E_t$ is detected in the coronal tomographic image, five voxels of (x, y, z), (x−1, y, z), (x+1, y, z), (x, y, z−1), and (x, y, z+1) are obtained. Further, when the sight line information $E_t$ is detected in the sagittal tomographic image, five voxels of (x, y, z), (x, y−1, z), (x, y+1, z), (x, y, z−1), and (x, y, z+1) are obtained.

Note that the timing to execute the above-described processing of expanding the position of an observed voxel is not limited to step S602. For example, it is also possible to obtain only sight line information in step S602, and expand the voxel position $O_{tp}$ of observation region information in step S604 by referring to the display content $O_{td}$, or expand it at another timing. An example of expanding a voxel position in step S604 will be explained in more detail in the fifth embodiment.

(Modification 4-2)

In the fourth embodiment, in step S604, the identification condition is "$O_{tp}$ that has appeared once or more is identified as an observed voxel regardless of $O_{td}$ in the observation region information $O_t$". However, the identification condition is not limited to this. For example, the attention time of a doctor in radiogram interpretation may be considered, and a region where the accumulated time or accumulated count for or at which the gaze position was detected in a tomographic image exceeds the first threshold may be identified as an observed region in a three-dimensional medical image. In this case, for example, a region where the accumulated time of observation in a tomographic image is equal to or longer than the first threshold may be identified as an observed region in a three-dimensional medical image. For example, when the first threshold is 3 sec, if the sampling rate is 0.1 sec, it is determined that a region having $O_{tp}$ that has appeared 30 times or more in observation region information has been observed.

Alternatively, the residence time of the sight line may be considered, and a region where the time for which the gaze position was continuously detected in a tomographic image exceeds the second threshold may be identified as an observed region in a three-dimensional medical image. For example, when the second threshold is 1 sec, a region observed continuously for 1 sec or more in each tomographic image is regarded as an observed region (pixel) in this tomographic image, and is identified as an observed region (voxel) in a three-dimensional medical image. Note that the numerical values cited here are merely examples for the explanation, and the present invention is not limited to these numerical values, as a matter of course. A state in which the count of continuous observation for a predetermined time or more is equal to or larger than a predetermined count may be adopted as the identification condition for identifying a region as "observed".

An example (a region continuously observed for 1 sec or more is identified as an observed region) of the identification condition using the second threshold will be described in detail with reference to FIGS. 12A to 12C. FIG. 12A shows observation region information obtained at a sampling rate of 0.1 sec. In this example, (2, 2, 1) is continuously observed in an axial tomographic image in pieces of observation region information $O_2$ to $O_{13}$. This is equivalent to 1.2-sec continuous observation, so (2, 2, 1) is identified as "observed" in the axial tomographic image. To the contrary, a pixel corresponding to a voxel position (1, 1, 1) is continuously observed in a coronal tomographic image in pieces of observation region information $O_{202}$ to $O_{205}$ and a sagittal tomographic image in $O_{206}$ to $O_{213}$. In this case, (1, 1, 1) is observed continuously for 1.2 sec, but observed for 0.4 sec in the coronal tomographic image and for 0.8 sec in the sagittal tomographic image. Thus, the voxel position (1, 1, 1) is not observed continuously for 1 sec or more in the respective tomographic images, and is not identified as an observed region in either tomographic image. Considering this, FIG. 12B shows regions identified as observed regions in the respective tomographic images. FIG. 12C shows regions identified as observed regions in the three-dimensional medical image based on this table.

Fifth Embodiment

In the fourth embodiment, a region identified as "observed" in a tomographic image in one of all the tomographic directions is identified as an observed region in an entire three-dimensional medical image. In the fifth embodiment, when the same region in tomographic images in a plurality of tomographic directions out of all the tomographic directions has been observed, this region is identified as an observed region in an entire three-dimensional medical image. According to the fifth embodiment, when the same region has been observed in an axial tomographic image and a coronal tomographic image, it is identified as an observed region in a three-dimensional medical image. To the contrary, a region observed in only the axial tomographic image or the coronal tomographic image is not identified as an observed region in the three-dimensional medical image. Note that the arrangement of an image diagnosis assistance apparatus 10 according to the fifth embodiment is the same as that in the fourth embodiment. Assume that each functional component of a control unit 38 is implemented by software, as in the fourth embodiment. Processing according to the fifth embodiment will be explained with reference to the flowchart of FIG. 6.

Processes in steps S600 to S603 and S605 are the same as those in the fourth embodiment. In step S604, based on the identification condition and the generation condition, a marker generation unit 47 generates a marker to be displayed on an image by using observation region information obtained in step S602. In this embodiment, the identification condition is "a region that is determined to have been observed in each tomographic image and has been observed in a plurality of tomographic images is identified as an observed region in a three-dimensional medical image". The generation condition is "a voxel identified as an observed region is targeted". Further, a marker is implemented by superposing and displaying, on a tomographic image, a layer in which a pixel at a portion corresponding to an observed region in each tomographic image is colored in green.

Figure 13:
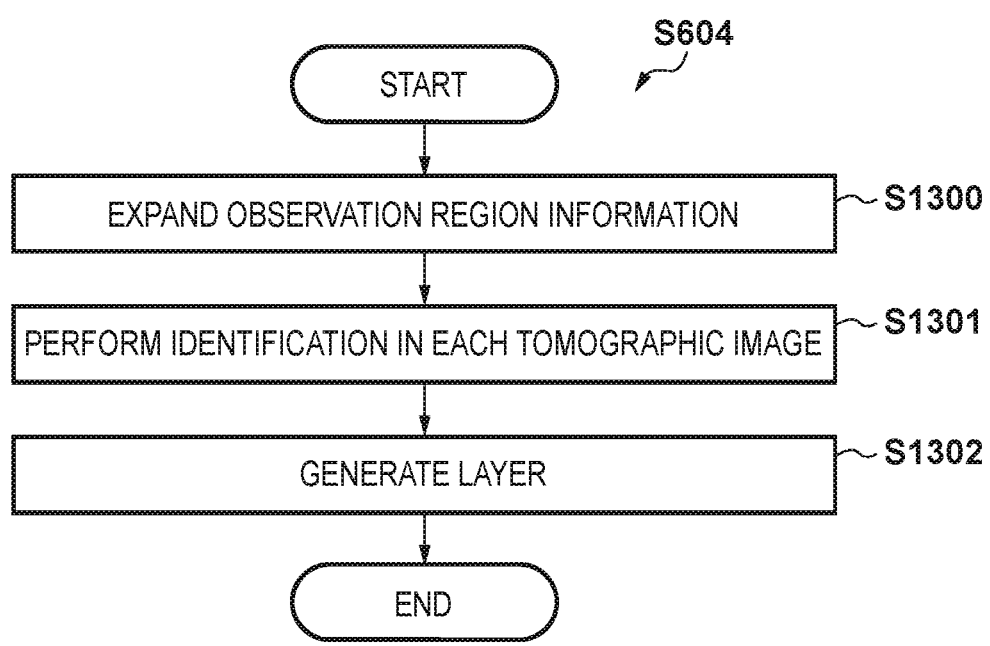
FIG. 13 is a flowchart for explaining part of processing according to the fifth embodiment.

Detailed processing in step S604 according to the fifth embodiment will be explained with reference to the flowchart of FIG. 13. In step S1300, the marker generation unit 47 expands observation region information $O_r$. More specifically, in consideration of the field of view, voxels vindicated by pixels within a distance of 1 from the center $O_{tp}$ within the plane of a tomographic image represented by $O_{td}$ are defined as $O_{tp}'$. In step S1301, the marker generation unit 47 determines an observed region (pixel) in each tomographic image based on the observation region information expanded in step S1300. In this embodiment, a region observed continuously for 1 sec or more in the same tomographic image (same $O_{td}$) is determined as an observed region (pixel) in the tomographic image.

Figure 14:
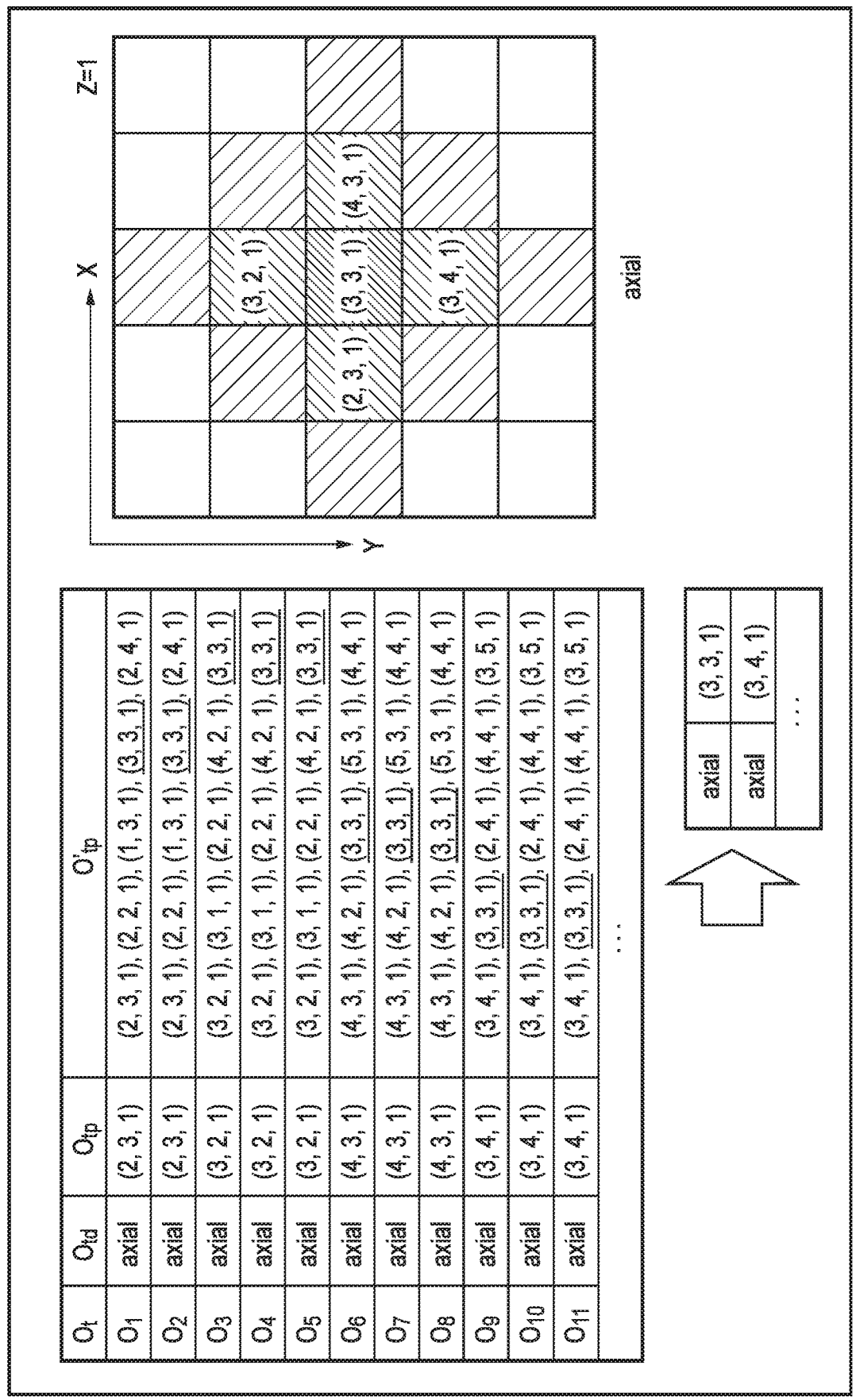
FIG. 14 is a view for explaining an identification condition according to the fifth embodiment.

A concrete example will be explained with reference to FIG. 14. FIG. 14 shows expanded observation region information, and an example in which an observed region in an axial tomographic image is determined. For example, in $O_1$, $O_{1p}(2, 3, 1)$ is expanded to $O'_{1p}\{(2, 3, 1) (2, 2, 1) (1, 3, 1) (3, 3, 1) (2, 4, 1)\}$ in consideration of the field of view. Another observation region information is also expanded as represented by the table shown in FIG. 14. When the sampling rate is 0.1 sec, a region observed continuously 10 times or more is a region observed continuously for 1 sec or more. In the example shown in FIG. 10, (3, 3, 1) is continuously observed from $O_1$ to $O_{11}$, and (3, 3, 1) is determined as an observed region in the axial tomographic image. When the field of view is taken into consideration, as in this example, even a pixel (voxel) that has not become $O_{tp}$ (that is, the center of the field of view) even once is sometimes determined as an observed region based on $O'_{tp}$.

In step S1302, the marker generation unit 47 identifies an observed region in a three-dimensional medical image based on the observed regions in the respective tomographic images that have been determined in step S1301. In accordance with the identification result, the marker generation unit 47 generates a layer (marker). In this embodiment, a region determined to have been observed in two or more tomographic images out of the axial tomographic image, the coronal tomographic image, and the sagittal tomographic image is identified as an observed region in the three-dimensional medical image. A table shown in FIG. 15 represents whether to generate a layer depending on whether a given voxel is determined to have been observed in respective tomographic images. When generating a layer in accordance with this table, the marker generation unit 47 generates a layer in which a pixel corresponding to the voxel in the respective tomographic images is colored in green.

FIG. 16 shows an example of a screen in which a marker generated by the marker generation unit 47 according to the fifth embodiment is superposed and displayed. This example is a display in which a green marker is added to a region identified as "observed" in a plurality of tomographic images, and no green marker is added to a region not identified as "observed" in any tomographic image or identified as "observed" in only one tomographic image. In FIG. 16, markers 1601 are green markers and indicate observed regions. Tomographic images have regions 1602 and 1603 where no green marker exists. The unobserved region 1602 appears in all the axial, coronal, and sagittal tomographic images during display. Note that the unobserved region 1603 appears in only a coronal tomographic image 702 (X-Z plane) owing to the extraction position of each tomographic image.

As described above, in the image diagnosis assistance apparatus 10 according to the fifth embodiment, the same region observed in a plurality of tomographic images can be identified as an observed region in a three-dimensional medical image, and information can be visualized and displayed based on the observed region. That is, a region that should be checked in a plurality of tomographic images is not identified as "observed" based on only observation in an individual tomogram. Hence, a high-quality radiogram interpretation omission preventing function can be provided efficiently.

Note that the fifth embodiment has explained the identification condition that a region observed in at least two tomographic images out of a plurality of tomographic images is identified as an observed region in a three-dimensional medical image. Although a combination of tomographic images in the identification condition is not limited, a combination of tomographic images may be limited. For example, a region observed in both an axial tomographic image and a sagittal tomographic image may be identified as an observed region in a three-dimensional medical image, and a combination of other tomographic images may not be used. Alternatively, the identification condition may be limited to, as a combination of tomographic images, a combination including specific tomographic images such as an axial tomographic image and a sagittal or coronal tomographic image.

(Modification 5-1)

In this embodiment, in step S605, the identification condition is "a region that is determined to have been observed in each tomographic image and has been observed in a plurality of tomographic images is identified as an observed region in a three-dimensional medical image", but is not limited to this. For example, instead of using observation results in a plurality of tomographic images, a region observed a plurality of times in the same tomographic image may be identified as an observed region in a three-dimensional medical image. In this case, the identification condition is "a region that is determined to have been observed in each tomographic image and has been observed a plurality of times in each tomographic image is identified as an observed region in a three-dimensional medical image". For example, a region where continuous detection of the gaze position for 1 sec or more in an axial tomographic image has been performed twice or more is identified as an observed region in a three-dimensional medical image.

Alternatively, when an observed region is determined in each tomographic image, the determination condition may change for each tomographic image. For example, radiogram interpretation is performed generally using an axial tomographic image. Considering this, a region where the gaze position has been detected continuously for 1 sec or more in an axial tomographic image and continuously for 0.5 sec or more in a coronal tomographic image and a sagittal tomographic image may be determined as an observed region in the respective tomographic images.

The identification condition may change depending on a region in one tomographic image. For example, the control unit 38 analyzes a medical image, extracts a region where an abnormal shadow is captured, and changes the identification condition depending on whether the target region is the extracted region. For example, when the extracted region has been observed in a plurality of tomographic images, it is identified as an observed region in a three-dimensional medical image. When another region has been observed in any of the tomographic images, it is identified as an observed region in the three-dimensional medical image. Alternatively, the control unit 38 analyzes a medical image, divides a tomographic image into regions based on the organ or structure, and changes the identification condition in accordance with the divided region. For example, when a lung parenchyma region out of the divided regions has been observed in a plurality of tomographic images, it is identified as an observed region in a three-dimensional medical image. When another region has been observed in any of the tomographic images, it is identified as an observed region in the three-dimensional medical image. Note that these are merely examples, and the present invention is not limited to these examples.

Sixth Embodiment

In the fourth and fifth embodiments, a marker is generated based on a predetermined identification condition and generation condition, and superposed and displayed on an image. In an image diagnosis assistance apparatus according to the sixth embodiment, a plurality of types of identification results are generated based on an identification condition and generation condition designated by a user, and these identification results are simultaneously superposed and displayed using a plurality of markers. Note that the arrangement of an image diagnosis assistance apparatus 10 according to this embodiment is the same as that in the fourth embodiment. Assume that each component is implemented by software, as in the fourth embodiment. Processing of the image diagnosis assistance apparatus 10 according to the sixth embodiment will be explained with reference to the flowchart of FIG. 6.

Processes in steps S600 to S602 are the same as those in the fourth embodiment. In step S603, a determination unit 46 determines, from an input from the user via an operation unit 35, whether radiogram interpretation has ended. When neither the identification condition nor the generation condition is designated by the user at this time, it is determined that radiogram interpretation has not ended. Determination of whether radiogram interpretation has ended is performed at a specific sampling rate. If the determination unit 46 determines that radiogram interpretation has not ended, the processes in steps S601 and S602 are repeated. If the determination unit 46 determines that radiogram interpretation has ended, the process advances to step S604.

Designation of the identification condition and generation condition by the user and determination of the end of radiogram interpretation are performed using a GUI as shown in FIG. 17. The GUI according to this embodiment has a designation area 1700 for designating a combination of tomographic images, in order to identify an observed region in a three-dimensional medical image. In the designation area 1700, whether each combination serves as an "observed" determination target, and the generation condition of a marker can be designated for each of eight combinations formed from an axial tomographic image, a coronal tomographic image, and a sagittal tomographic image. In the designation area 1700, check boxes of three values no marker, "marker to an observed region", and "marker to an unobserved region" are arranged for the above-mentioned eight combinations to designate the identification condition and the marker generation condition.

For example, in an item 1701, "observed" is checked in "coronal tomographic image and sagittal tomographic image". In this case, it is designated to identify a region observed in both a coronal tomographic image and a sagittal tomographic image as an observed region in a three-dimensional medical image, and generate a marker for the identified region. In an item 1702, "unobserved" is checked in "axial tomographic image". In this case, it is designated to discriminate an observed region in an axial tomographic image, and generate a marker for a region discriminated as "unobserved" (that is, a region other than a region discriminated as "observed" in an axial tomographic image). In an item 1703, "observed" is checked in "axial tomographic image and coronal tomographic image". As the processing content, a sagittal tomographic image in the item 1701 is replaced with an axial tomographic image. In the designation area 1700, a plurality of conditions can be simultaneously designated, as shown in FIG. 17.

When a radiogram interpretation end button 303 is clicked, radiogram interpretation end determination by the determination unit 46 is performed, and superposition and display of a marker are executed in accordance with a condition designated in the designation area 1700. When all conditions are not checked (that is, no marker is generated), it is not determined that radiogram interpretation has ended even if the radiogram interpretation end button 303 is clicked.

In step S604, based on the identification condition and generation condition designated in the designation area 1700, a marker generation unit 47 generates a marker to be displayed on an image by using observation region information obtained in step S602. In this embodiment, layers of different colors are assigned to each identification condition and each generation condition designated in the designation area 1700, and are superposed and displayed. A layer of a color assigned to a condition is superposed and displayed on a pixel of each tomographic image that corresponds to a voxel satisfying the condition.

When a plurality of conditions are simultaneously satisfied, layers assigned to the respective conditions are simultaneously superposed and displayed. For example, a case will be examined, in which two conditions, that is, an "observed" region in "coronal tomographic image and sagittal tomographic image" and an "unobserved" region in "axial tomographic image" are designated. In this case, layers of two colors are superposed and displayed in a region that has not been observed in an axial tomographic image but has been observed in a coronal tomographic image and a sagittal tomographic image. As a result, a marker of a color as a mixture of these two colors is displayed.

Figure 18:
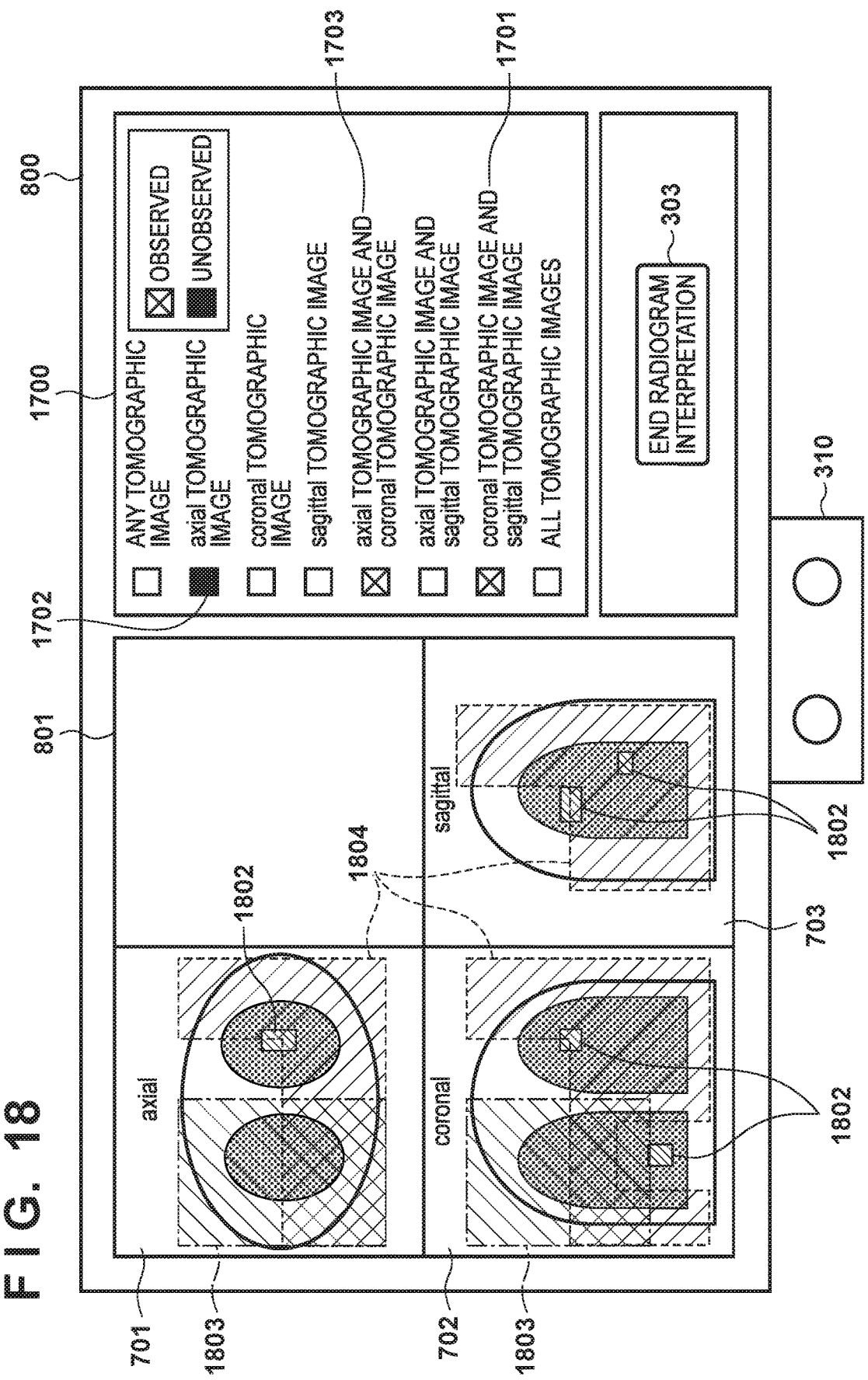
FIG. 18 is a view showing an example of superposition and display of a marker according to the sixth embodiment.

In step S605, a display processing unit 42 displays, on a display unit 36, medical information obtained in step S600 and the markers generated in step S604. FIG. 18 shows an example of a screen in which designation of the identification condition and generation condition, and superposition and display of a marker according to this embodiment are performed. This example is an example of generation and display of a marker in accordance with the settings (items 1701 to 1703) shown in FIG. 17. The display processing unit 42 according to the sixth embodiment identifiably displays a region identified as "observed" or another region (unobserved region) in accordance with each designation in the designation area 1700. In this display, the display processing unit 42 presents a display of a different form for each designated tomographic image or tomographic image combination in accordance with an observed region or an unobserved region. In the display example of FIG. 18, a red layer 1802 is superposed and displayed in a region corresponding to "unobserved" in "axial tomographic image", and a blue layer 1803 is superposed and displayed in a region corresponding to "observed" in "axial tomographic image and coronal tomographic image". Further, a green layer 1804 is superposed and displayed in a region corresponding to "observed" in "coronal tomographic image and sagittal tomographic image".

The user looks, for example, a region where the layers 1802 and 1804 overlap each other, and can easily grasp that this region has been "not observed in an axial tomographic image but observed in a coronal tomographic image and a sagittal tomographic image". In other words, the AND condition and OR condition of a plurality of conditions designated in the designation area 1700 can be easily grasped on the screen.

As described above, in the diagnosis assistance apparatus according to the sixth embodiment, the user can designate an identification condition and a generation condition. It is also possible to simultaneously designate a plurality of conditions and simultaneously perform superposition and display. A condition the user wants to recognize can be designated, markers of different conditions can be simultaneously presented, and the radiogram interpretation situation can be easily grasped. Thus, radiogram interpretation omission can be prevented efficiently.

(Modification 6-1)

In this embodiment, a plurality of conditions can be designated using check boxes in the designation area 1700, but another method is also possible. For example, it is also possible to input a condition by a natural language, perform natural language processing using an analysis apparatus (not shown), and extract the condition. Only one condition may be designated using a radio button. Alternatively, a combo box may be prepared so that an arbitrary number of conditions can be selected from the combo box. Alternatively, the name (for example, axial, coronal, or sagittal) of each tomographic image and a general logical operation expression (for example, AND, OR, NAND, NOR, or NOT) may be used so that a condition can be designated. Needless to say, the present invention is not limited to these examples.

(Modification 6-2)

In this embodiment, layers of different colors are assigned in advance to all identification conditions and generation conditions in step S605. However, another method is also possible. For example, the user may be able to arbitrarily set the color or shape of a marker corresponding to a condition. In this case, a function of generating a marker for each condition by the user may be separately arranged.

(Modification 6-3)

When the user selects a generation condition to generate a marker for an "unobserved" region under any identification condition, and a marker is generated under the generation condition, a warning may be generated. That is, when there is a region identified as "unobserved" under a set identification condition, a warning may be generated. The warning display may be presented by a GUI such as a message box, or a beep sound may be output. The timing to generate a warning may be the timing to generate a marker, or the timing to end radiogram interpretation. Alternatively, a mechanism that inhibits the end of radiogram interpretation until no "unobserved" region remains any more may be adopted. Note that the above-described method may be applied to a predetermined identification condition.

Seventh Embodiment

The fourth to sixth embodiments have been explained by exemplifying a case in which tomographic images of a three-dimensional medical image in a plurality of tomographic directions perpendicular to each other are displayed and interpreted. However, the present invention is not limited to this form, and even a difference other than the tomographic direction difference is applicable as long as a plurality of images are constructed from the same three-dimensional medical image. The seventh embodiment will describe an example in which radiogram interpretation is performed using two axial tomographic images of different display conditions. The display condition described in the seventh embodiment represents not the type (tomographic direction) of a tomographic image, but the window level WL and window width WW. As a matter of course, the display condition is not limited to this.

The arrangement of an image diagnosis assistance apparatus 10 according to the seventh embodiment is the same as that in the fourth embodiment. Assume that each component is implemented by software, as in the fourth embodiment. Processing according to the seventh embodiment will be explained with reference to the flowchart of FIG. 6. However, a display content Disp included in observation region information is not the above-described information representing one of axial, coronal, and sagittal tomographic images, but information representing a display condition under which a tomographic image is displayed. The following description handles two display conditions, that is, the lung field condition (WL: −600/WW: 1500) and the mediastinal condition (WL: 35/WW: 350). The identification condition is "a region observed in a tomographic image under either display condition is identified as an observed region in a three-dimensional medical image".

Processes in steps S600 and S601 are the same as those in the fourth embodiment. In step S602, a recording unit 45 records observation region information corresponding to sight line information by using the sight line information obtained in step S601. For example, assume that WL: −600/WW: 1500 as the display content Disp and (100, 150, 140) as position information Pos are associated with a pixel (370, 290) represented by sight line information $E_1$. In this case, $O_{1d}$: (WL: −600/WW: 1500) and $O_{1p}$(100, 150, 140) are obtained as observation region information $O_1$. Processing in step S603 is the same as that in the fourth embodiment.

In step S604, based on the identification condition and the generation condition, a marker generation unit 47 generates a marker to be displayed on an image by using the observation region information obtained in step S602. According to the above-mentioned identification condition, $O_{tp}$ that has appeared once or more is identified as an observed region regardless of $O_{td}$ in the observation region information $O_t$. That is, a region where the gaze position has been detected even once in a tomographic image is identified as an observed region (voxel) in a three-dimensional medical image regardless of the display condition. Note that the generation condition, the marker type, and processing in step S605 are the same as those in the fourth embodiment.

FIG. 19 shows an example of a screen including a display example of a medical image according to the seventh embodiment. For example, an axial tomographic image 1901 displayed under the lung field condition, and an axial tomographic image 1902 displayed under the mediastinal condition are displayed in an image display area 1900. For example, when an observed region is identified in the axial tomographic image 1901 displayed under the lung field condition, a region (voxel) of a three-dimensional medical image that corresponds to this region is identified as "observed". In the screen display of FIG. 19, markers 1903 generated by the marker generation unit 47 are superposed and displayed on the axial tomographic image 1901 displayed under the lung field condition and the axial tomographic image 1902 displayed under the mediastinal condition, respectively.

Note that the identification condition may be "a region that has been observed in both tomographic images displayed under the lung field condition and the mediastinal condition is identified as an observed region in a three-dimensional medical image". In this case, a region observed in only an axial tomographic image displayed under the lung field condition is not identified as an observed region in a three-dimensional medical image. However, if it is detected that this region has been observed even in a tomographic image (which may be a tomographic image other than an axial one) displayed under the mediastinal condition, this region is identified as an observed region in the three-dimensional medical image. The condition may be that a region is observed in tomographic images of the same type under two different display conditions. In this case, a region observed in both axial tomographic images displayed under, for example, the lung field condition and the mediastinal condition is identified as an observed region in a three-dimensional medical image. However, a region only observed in an axial tomographic image under the lung field condition and a sagittal tomographic image under the mediastinal condition is not identified as an observed region in the three-dimensional medical image.

As described above, in the image diagnosis assistance apparatus according to the seventh embodiment, when a given region is observed regardless of a display condition under which the region has been observed, a corresponding region in a three-dimensional medical image is identified as an observed region, and information can be visualized and displayed based on the observed region. That is, since even a region interpreted in an image under a different display condition is not identified as "unobserved" as a whole, and radiogram interpretation omission can be prevented efficiently.

(Modification 7-1)

In the seventh embodiment, information (display content Disp) representing a display condition under which each pixel Pix on the screen is displayed is stored as display information. However, another information may also be stored. For example, when the display area is divided and used as in the image display area 801 or the image display area 1900, an ID may be assigned to each divided area and an ID may be saved in the display content Disp. More specifically, is assigned to an area where an axial tomographic image under the lung field condition is displayed, and is assigned to an area where an axial tomographic image under the mediastinal condition is displayed. These values are then saved. According to this method, even when the display condition is changed during image display, whether the target region is an observed region can be identified based on the information of the divided area. Hence, radiogram interpretation omission can be prevented efficiently by a more flexible method.

(Modification 7-2)

The seventh embodiment has explained an example of adapting the present invention to a form in which a plurality of images constructed from the same three-dimensional medical image are displayed and interpreted. However, the present invention can also be adapted to another three-dimensional medical image reconstructed using another reconstruction function for the same projection data. In general, a CT image created in an X-ray CT apparatus is obtained by convoluting a predetermined reconstruction function and projection data obtained by imaging an object. The design of the reconstruction function is arbitrary, and a reconstruction function appropriate for the clinical purpose is used. In some cases, a plurality of CT images are created using a plurality of reconstruction functions for the same projection data. For example, in the case of a chest CT image, a lung field condition reconstructed image and a mediastinal condition reconstructed image are generally created. The lung field condition reconstructed image is a medical image created using a reconstruction function suited to observing the inside of the lung field. The mediastinal condition reconstructed image is a medical image created using a reconstruction function suited to observing the mediastinal space.

In this modification, it is only necessary that the axial tomographic image 1901 displayed under the lung field condition in FIG. 19 is adapted as the lung field condition reconstructed image, and the axial tomographic image 1902 displayed under the mediastinal condition is adapted as the mediastinal condition reconstructed image.

Note that the first to seventh embodiments and their modifications described above can be properly combined.

According to the above-described embodiments, an observed region and an unobserved region in a three-dimensional medical image can be more appropriately identified based on an observed region in a tomographic image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-102725, filed May 16, 2014 which is hereby incorporated by reference herein in its entirety.

The invention claimed is:

1. An image diagnosis assistance apparatus comprising:
a memory storing a program; and
one or more processors which, by executing the program, function to:
(a) control display, on a display screen, of a plurality of tomographic images in different tomographic directions, obtained from a three-dimensional medical image;
(b) detect a gaze position of a user on the display screen;
(c) determine an observed region in the plurality of tomographic images based on the detected gaze position; and
(d) identify, as an observed region, a region determined to have been observed in at least two tomographic images having different tomographic directions out of the plurality of tomographic images obtained from the three-dimensional medical image.

2. The apparatus according to claim 1, wherein the one or more processors determines, as the observed region, (a) a pixel in which the gaze position has been detected in a tomographic image, and (b) pixels within a predetermined distance from the pixel in the tomographic image.

3. The apparatus according to claim 1, wherein the one or more processors determines, as the observed region, a region where an accumulated time for which the gaze position was detected in a tomographic image exceeds a threshold.

4. The apparatus according to claim 3, wherein the one or more processors uses different thresholds in accordance with a region extracted from a tomographic image or a region obtained by dividing the tomographic image.

5. The apparatus according to claim 1, wherein the one or more processors determines, as the observed region, a region where a count at which the gaze position was detected in a tomographic image exceeds a threshold.

6. The apparatus according to claim 1, wherein the one or more processors determines, as the observed region, a region where a time for which the gaze position was continuously detected in a tomographic image exceeds a threshold.

7. The apparatus according to claim 1, wherein the one or more processors uses different thresholds for respective tomographic images obtained from the three-dimensional medical image.

8. The apparatus according to claim 1, wherein the one or more processors, by executing the program, further control display of a region identified as the observed region or another region so as to allow a user to identify the region.

9. The apparatus according to claim 1, wherein the one or more processors, by executing the program, further designate, from the plurality of tomographic images, at least one tomographic image or a combination of tomographic images to be used for the determination.

10. The apparatus according to claim 9, wherein the designation further designates, for each designated tomographic image or tomographic image combination, which of a region identified as observed and a region identified as unobserved displays a marker.

11. The apparatus according to claim 10, wherein the one or more processors, by executing the program, further (a) control display of a region identified as the observed region or another region so as to allow a user to identify the region, (b) control display of a region identified as the observed region or another region in accordance with designation by the designation, and (c) control display of a region in a different form for each designated tomographic image or tomographic image combination in accordance with an observed region or an unobserved region.

12. The apparatus according to claim 1, wherein the plurality of tomographic images include an axial tomographic image, a sagittal tomographic image, and a coronal tomographic image.

13. A control method of an image diagnosis assistance apparatus, the control method comprising:
displaying, on a display screen, a plurality of tomographic images in different tomographic directions obtained from a three-dimensional medical image;
detecting a gaze position of a user on the display screen;
determining an observed region in the plurality of tomographic images based on the gaze position; and
identifying, as an observed region, a region determined to have been observed in at least two tomographic images having different tomographic directions out of the plurality of tomographic images obtained from the three-dimensional medical image.

14. A non-transitory computer-readable storage medium storing a program for causing a computer to execute the control method according to claim 13.

* * * * *